(12) United States Patent
Langlade Demoyen et al.

(10) Patent No.: US 11,634,494 B2
(45) Date of Patent: *Apr. 25, 2023

(54) ANTI HLA-G SPECIFIC ANTIBODIES

(71) Applicant: Invectys SA, Paris (FR)

(72) Inventors: Pierre Langlade Demoyen, Neuilly-sur-Seine (FR); Thierry Huet, Nogent sur Marne (FR); Julien Caumartin, Le Vésinet (FR); Maria Loustau, Paris (FR); Maria Wehbe, Montigny-le-Bretonneux (FR)

(73) Assignee: Invectys SA, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,483

(22) Filed: Apr. 25, 2022

(65) Prior Publication Data

US 2022/0251216 A1 Aug. 11, 2022

Related U.S. Application Data

(63) Continuation of application No. 17/466,607, filed on Sep. 3, 2021, now Pat. No. 11,312,774, which is a continuation of application No. 17/080,017, filed on Oct. 26, 2020, now Pat. No. 11,111,302, which is a continuation of application No. 16/306,267, filed as application No. PCT/EP2017/063503 on Jun. 2, 2017, now abandoned.

(30) Foreign Application Priority Data

Jun. 3, 2016 (EP) .................................. 16305650

(51) Int. Cl.
| | | |
|---|---|---|
| C07K 16/00 | (2006.01) | |
| C07K 16/28 | (2006.01) | |
| C07K 7/08 | (2006.01) | |
| A61P 31/12 | (2006.01) | |
| A61P 35/00 | (2006.01) | |
| C07K 7/50 | (2006.01) | |

(52) U.S. Cl.
CPC .......... *C07K 16/2833* (2013.01); *A61P 31/12* (2018.01); *A61P 35/00* (2018.01); *C07K 7/08* (2013.01); *C07K 7/50* (2013.01); *C07K 2317/33* (2013.01); *C07K 2317/34* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 10,800,847 | B2 | 10/2020 | Ravindranath et al. |
| 11,111,302 | B2 | 9/2021 | Langlade Demoyen et al. |
| 11,312,774 | B2 | 4/2022 | Langlade Demoyen et al. |
| 2019/0233520 | A1 | 8/2019 | Langlade Demoyen et al. |
| 2020/0102389 | A1 | 4/2020 | Fischer et al. |
| 2021/0054081 | A1 | 2/2021 | Langlade Demoyen et al. |
| 2021/0070864 | A1 | 3/2021 | Epstein et al. |
| 2021/0309748 | A1 | 10/2021 | Langlade Demoyen et al. |

FOREIGN PATENT DOCUMENTS

| CN | 1718588 A | 1/2006 |
| CN | 101967191 A | 2/2011 |
| CN | 102086459 A | 6/2011 |
| EP | 2184070 A1 | 5/2010 |
| EP | 2264067 A1 | 12/2010 |
| WO | WO 1996/31604 A1 | 10/1996 |
| WO | WO 2008/121894 A2 | 10/2008 |
| WO | WO 2014/072534 A1 | 5/2014 |

OTHER PUBLICATIONS

Bensussan, A. et al., "Detection of Membrane-Bound HLA-G Translated Products with a Specific Monoclonal Antibody," Proc. Natl. Acad. Sci. (1995) vol. 92, pp. 10292-10296.
Casset et al., "A peptide mimetic of an anti-CD4 monoclonal antibody by rational design," Biochemical and Biophysical Research Communications (2003) 307, 198-205.
Chen et al., "Selection and Analysis of an Optimized Anti-VEGF Antibody: Crystal Structure of an Affinity-matured Fab in Complex with Antigen," J. Mol. Biol. (1999) 293, 865-881.
Chothia et al., "The relation between the divergence of sequence and structure in proteins," The EMBO Journal, 1986, vol. 5, No. 4, pp. 823-826.
Chumbley et al., "Generation of an antibody to HLA-G in transgenic mice and demonstration of the tissue reactivity of this antibody," J Reprod Immunol. Dec. 1994;27(3):173-186.
Clements et al., "Crystal structure of HLA-G: A nonclassical MHC class I molecule expressed at the fetal-maternal interface", PNAS, Mar. 2005, 102:9 3360-3365.
Communication (International Search Report and Written Opinion) issued by the International Searching Authority in International Patent No. PCT/EP2017/063503, dated Aug. 10, 2017, 21 pages total.

(Continued)

*Primary Examiner* — Jennifer E Graser

(74) *Attorney, Agent, or Firm* — Cooley LLP; Ivor R. Elrifi

(57) ABSTRACT

The present invention relates to antibodies, or antigen-binding fragments thereof, directed against human leukocyte antigen-G (HLA-G) protein and raised against an immunogenic peptide derived from the α3 domain of HLA-G protein. The invention further relates to the immunogenic peptide, and methods for producing said anti-HLA-G specific antibodies.

9 Claims, 12 Drawing Sheets

Specification includes a Sequence Listing.

(56) References Cited

OTHER PUBLICATIONS

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology (2002), 169: 3076-3084.

Desai et al., "Structural Relatedness of Distinct Determinants Recognized by Monoclonal Antibody TP25.99 on TP25.99 on β2-Microglobulin-Associated and β2-Microglobulin-Free HLA Class I Heavy Chains1," The Journal of Immunology, 2000,165, 3275-3283.

Greenspan et al., "Defining epitopes: It's not as easy as it seems," Nature Biotechnology, Oct. 1999, vol. 17, pp. 936-937.

Holm et al., "Functional mapping and single chain construction of the anti-cytokeratin 8 monoclonal antibody TS1," Molecular Immunology (2007) 44, 1075-1084.

Lin et al., "HLA-G expression in human ovarian carcinoma counteract NK cell function," Ann Oncol. 2007, 18(11):1804-1809.

MacCallum et al., "Antibody-antigen Interactions: Contact Analysis and Binding Site Topography," J. Mol. Biol. (1996), 262,732-745.

Mikayama et al., "Molecular cloning and functional expression of a cDNA encoding glycosylation-inhibiting factor," Proc. Natl. Acad. Sci. USA, Nov. 1993, vol. 90, pp. 10056-10060.

Rudikoff et al., "Single amino acid substitution altering antigen-binding specificity," Proc. Natl. Acad. Sci. USA, Mar. 1982, vol. 79, pp. 1979-1983.

Rudinger, J., "Characteristics of the amino acids as components of a peptide hormone sequence," Peptide Hormones (ed. Parsons), University Park Press, Jun. 1976, pp. 1-7.

Shiroishi, M. et al., "Human Inhibitory Receptors Ig-like Transcript 2 (ILT2) and ILT4 Compete with CD8 for MHC Class I Binding and Bind Preferentially to HLA-G" PNAS (2003) vol. 100, No. 15, pp. 8856-8861.

Vajdos et al., "Comprehensive Functional Maps of the Antigen-binding Site of an Anti-Erb82 Antibody Obtained with Shotgun Scanning Mutagenesis," J. Mol. Biol. (2002), 320, 415-428.

Wu et al., "Humanization of a murine monoclonal antibody by simultaneous optimization of framework and CDR residues," J. Mol. Biol. (1999) 294: 151-162.

Zhang, X. et al., "Methotrexate-Loaded PLGA Nanobubbles for Ultrasound Imaging and Synergistic Targeted Therapy of Residual Tumor During HIFU Ablation," Biomaterials (2014) vol. 35, pp. 5148-5161.

Zhang et al., "Research advances of soluble human leukocyte antigen G," Journal of International Reproductive Health/Family Planning, 2017, vol. 26, No. 6, English abstract only (1 page).

FIG. 1A

Domain α 1

```
HLA-G   GSHSMRYFSAAVSRPGRGEPRFIAMGYVDDTQFVRFDSDSACPRMEPRAPWVEQEGPEYWEEETRNTKAHAQTDRMNLQTLRGYYNQSEA
HLA-E   GSHSLKYFHTSVSRPGRGEPRFISVGYVDDTQFVRFDNDAASPRMVPRAPWMEQEGSEYWDRETRSARDTAQIFRVNLRTLRGYYNQSEA
HLA-A2  GSHSMRYFFTSVSRPGRGEPRFIAVGYVDDTQFVRFDSDAASQRMEPRAPWIEQEGPEYWDGETRNVKAHSQTHRVDLGTLRGYYNQSEA
HLA-B7  GSHSMRYFYTSVSRPGRGEPRFISVGYVDDTQFVRFDSDAASPREEPRAPWIEQEGPEYWDRNTQIYKAQAQTDRESLRNLRGYYNQSEA
HLA-B44 GSHSMRYFYTAVSRPGRGEPRFITVGYVDDTQFVRFDSDDTQFVRFDSDDESPRGEPRAPWVERRGPEYWDRETQKYKRQAQTDRVSLRNLRGYYNQSEA
HLA-CW3 GSHSMRYFYTAMSRPGRGEPRFIAVGYVDDTQFVRFDSDAASPRMEPRAPWIEQEGPEYWDRETQISKTNTQTFRENLRTALRYYNQSEA
Residues 1.......10........20........30........40........50........60........70........80.......90...
```

Domain α 2

```
HLA-G   SSHTLQWMIGCDLGSDGRLLRGYEQYAYDGKDYIALNEDLRSWTAADTAAQISKRKCEAANVAEQRRAYLEGTCVEWLHRYLENGKEMLQRA
HLA-E   GSHTLQWMHGCELGPDGRLRGYEQFAYDGKDYLTLNEDLRSWTAVDTAAQISEQKSNDASEAEHQRAYLEDTCVEWLHKYLEKGKETLLHL
HLA-A2  GSHTLQWRMYGCDVGSDWRFLRGYHQYAYDGKDYIALKEDLRSWTAADMAAQITKRKWEAAHVAEQRRAYLEGTCVEWLRRYLENGKDTLERA
HLA-B7  GSHTLQSMYGCDVGPDGRLLRGYHQYAYDGKDYIALNEDLRSWTAANTAAMTAAQITQRKWEAAREAEQRRAYLEGECVEWLRRYLENGKDKLERA
HLA-B44 GSHTIRMYGCDVGPDWMGCELGPDGRLLRGYDQHAVDGKDYIALNEDLRSWTAANTAAQITQRKWEAARVAARAAEQLRAYLEGTCVEWLRRYLENGKETLQRA
HLA-CW3 GSHTIQSMYGCDIGPDGRLLRGYHQDAYDGKDYIALNEDLSSWTAADTAAQITQRKWEAAVAEQDRAYLEGCVESLRRYLENGKETLQRA
Residues ...100.......110.......120.......130.......140.......150.......160.......170.......180...
```

Domain α 3

```
HLA-G   DPPKTHVTHHPVFDYEATLRCWALGFYPAEIILTWQRDGEDQTQDVELVETRPAGDGTFQKWAAVVVPSGEEQRYTCHVQHEGLPEPLMLRWK
HLA-E   EPPKTHVTHHPISDHEATLRCWALGFYPAEITLTWQRDGEDQTGDTEQDTELVETRPAGDGTFQKWAAVVVPSGEEQRYTCHVQHEGLPEPVTLRWK
HLA-A2  DAPKTHMTHHAVSDHEATLRCWALSFYPAEITLTWQRDGEDQTQDTELVETRPAGDGTFQKWAAVVVPSGEEQRYTCHVQHEGLPKPLTLRWE
HLA-B7  DPPKTHVTHHPISDHEATLRCWALGFYPAEIILTWQRDGEDQTQDTELVETRPAGDRTFQKWAAVVVPSGEEQRYTCHVQHEGLPKPLTLRWE
HLA-B44 EHPKTHVTHHPVSDHEATLRCWALGFYPAEITLTWQRDGEDQTQDTELVETRPAGDGTFQKWAAVVVPSGEEQRYTCHVQHEGLPEPLTLRWE
HLA-CW3 DPPKTHVTHHPTSDHEATLRCWALGFYPAEITLTWQRDGEDQTQDTELVETRPAGDRTFQKWAAVVVPSGEEQRYTCHVQHEGLPKPLILRWE
Residues ...190.......200.......210.......220.......230.......240.......250.......260.......270...
```

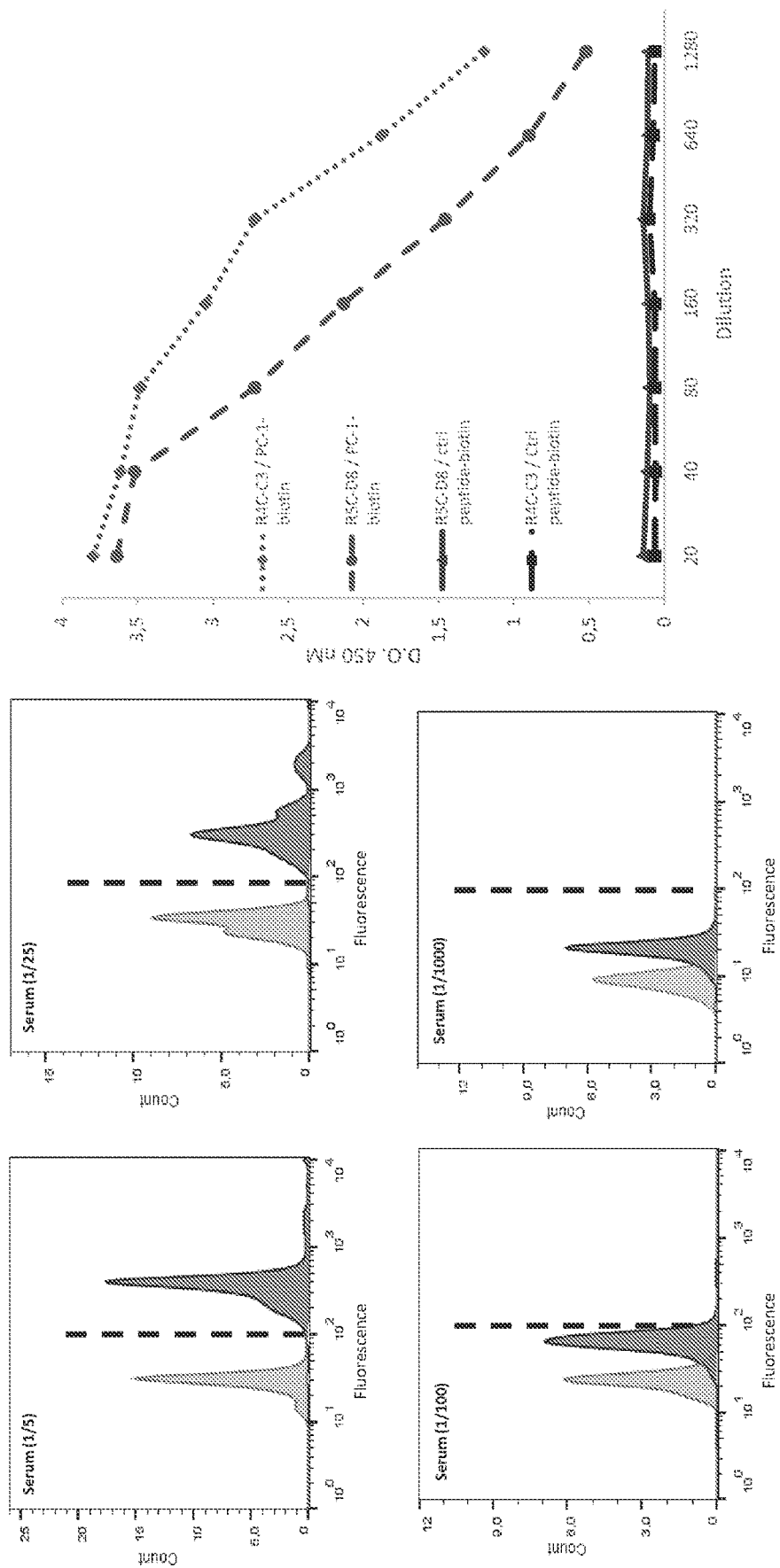

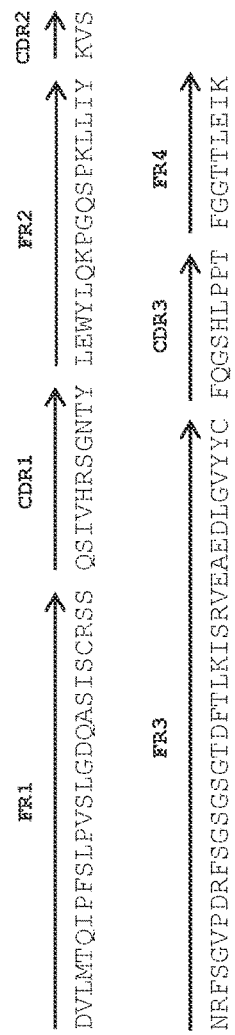

CAGGTCCAACTGCAGCAGCCTGGGGCTGAACTGGTGTGAGGCCTGAGGCCTCTTCAGTGAAGCTGTCCTGCAAGG
CTTCTGGCTACACCTTCACCGACTACTGGATGATTGGGTGAAGCAGAGGCCTGAAGGGCAAGGCCTTGAATG
GATTGGTACCATTTACCCTTCTGATAGTTCAACTCACTACAAGAAGTTCAAGGGCAAGGCCACACTG
ACTGTAGACAAATCCTCCAGCACAGCCTACATGCAGCTCAGCAGCCTGACATCTGAGGACTCTGCGGTC
ATTACTGTGCAAGAGAGGGACTAGCTGGGCTGTGTTCTACTTTTGACTACTGGGGCCAAGGCACCACTCTCAC
AGTCTCCTCA

```
        FR1                         CDR1              FR2
QVQLQQPGAELVRPGSSVKLSCKAS GYTFTDYW MDWVKQRPGQGLEWIGT
                FR3                                  CDR3            FR4
HYNQEFKGKATMTVDKSSSTAYMHLSSLTSEDSAVYYC AREGLAGVFYFDY WGQGTTLTVSS
```

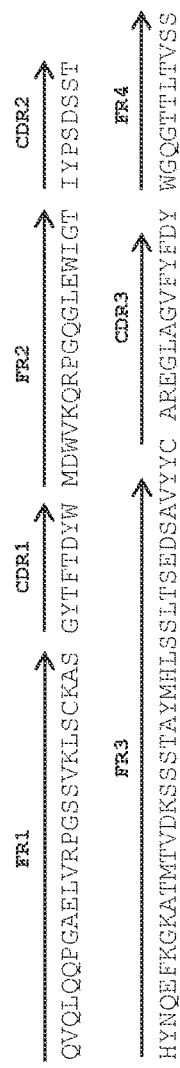

FIG. 3B

V-Gene allele:

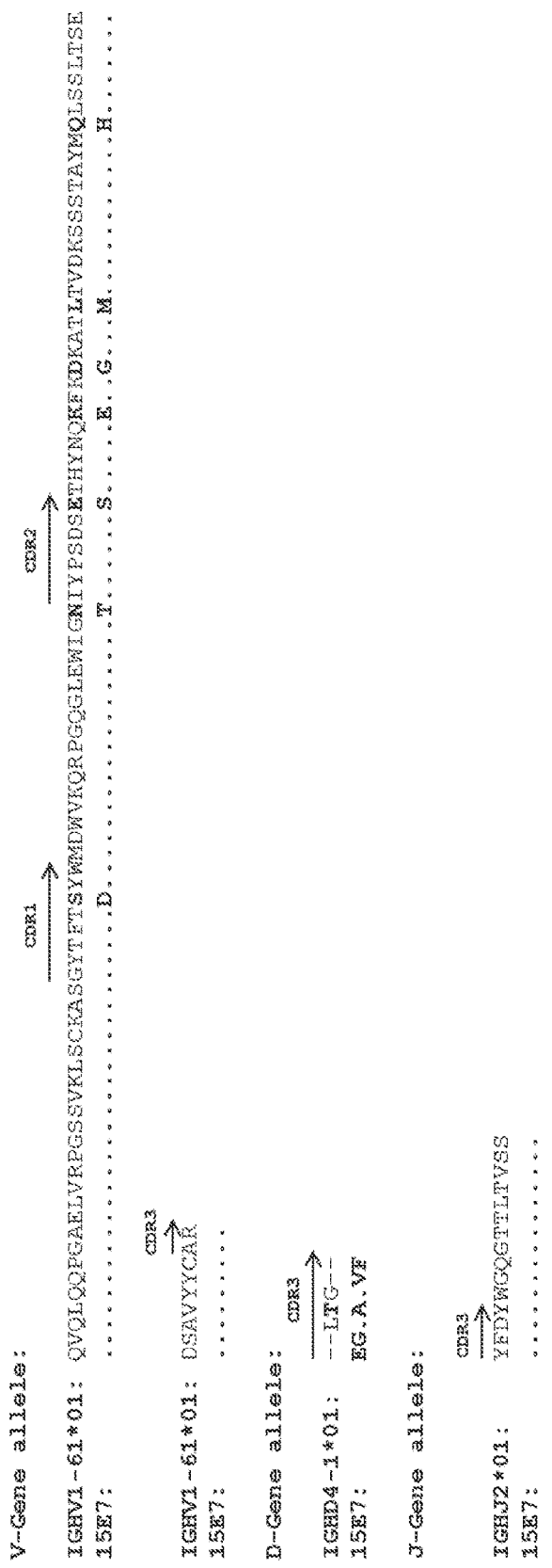

```
IGHV1-61*01:  QVQLQQPGAELVRPGSSVKLSCASGYTFTSYWMDWVKQRPGQGLEWIGNIYPSDSETHYNQKFKDKATLTVDKSSSTAYMQLSSLTSE
15E7:         ...................................D.........................T......S......E..G....M........H........

IGHV1-61*01:  DSAVYYCAR
15E7:         .........

D-Gene allele:

IGHD4-1*01:   --LTG--
15E7:         EG.A.VF

J-Gene allele:

IGHJ2*01:     YFDYWGQGTTLTVSS
15E7:         ...............
```

CAGGTGCAGCTGAAGCAGTCTGGGCCTGGGCCTGGTTAGGCCTCAGTGAAGATACCCTGCAAGCTT
CTGGTTACTCATTCATTCACCAACTACTGGATGCACTGGGTGAAGCAGAGACCACCTGAGTGGATTGG
CATGATTGCTCCTTCCGATAGTGATAGTGCAACTCAGAATTTCAAGGACAAGGCCACATTGACTGTAGAC
AAATCCTCCAGCACACGTACATGCAACTCAGCAGCCCGACATCTGAGGACTCTGCCGTCTATTACTGTGCAA
GAGAGGGAGTTACAATGATAACGACGGGCCTTGACTACTGGGGCCAAGGCACCACTCTCACAGTCTCCTCA

```
        FR1                          CDR1              FR2
QVQLKQSGPELVRPGASVKIPCKAS   GYSFTNYW   MHWVKQRPGQGLEWIGM
               FR3                                    CDR2      FR4
RLNQNFKDKATLTVDKSSSTAYMQLSSPTSEDSAVYYC AREGVTMITTGLDY  WGQGTTLTVSS
                                                      IAPSDSDS
```

FIG. 5B

V-Gene allele:

```
IGHV1S126-1:   QVQLQQPGAELVKPGASVKISCKASGYTFTSYWMNWVKQRPGQGLEWIGEIDPSDSYTNNQFKDKATLTVDKSSST
                                CDR1                                  CDR2
R4C-C3:        ....K.S..Q..R......P......S..N...H............M.A...DSRL..N..........

CDR3
IGHV1S126-1:   AYMQLSSLT-SEDSAVYYCAR
R4C-C3:        .......P.Q..........

D-Gene allele:                  CDR3
IGHD2-12*01:   PTTVT-IVT
R4C-C3:        -EG..M.T.

J-Gene allele:    CDR3
IGHJ2*01:      YEDYWGQGTTLTVSS
R4C-C3:        GL.............
```

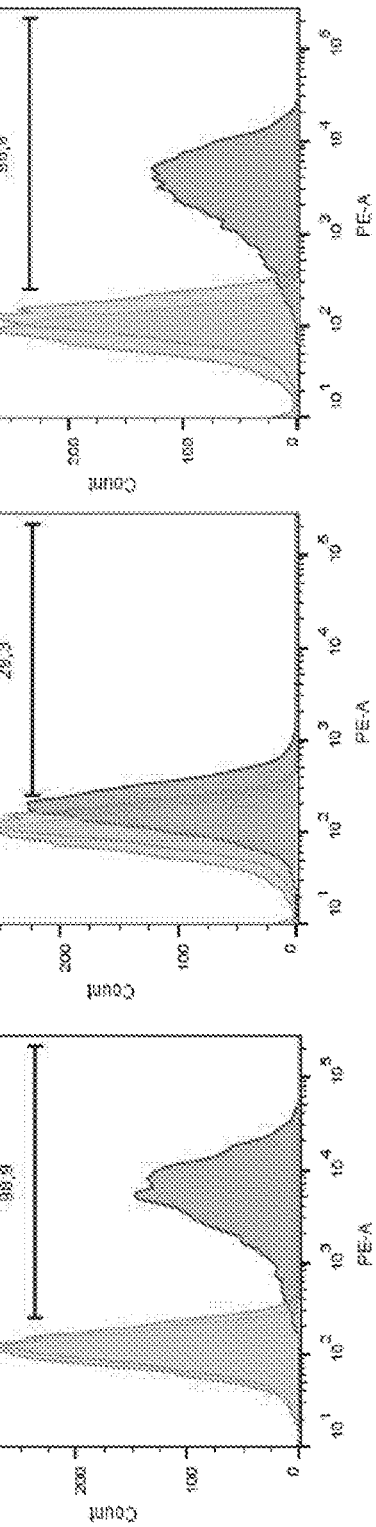
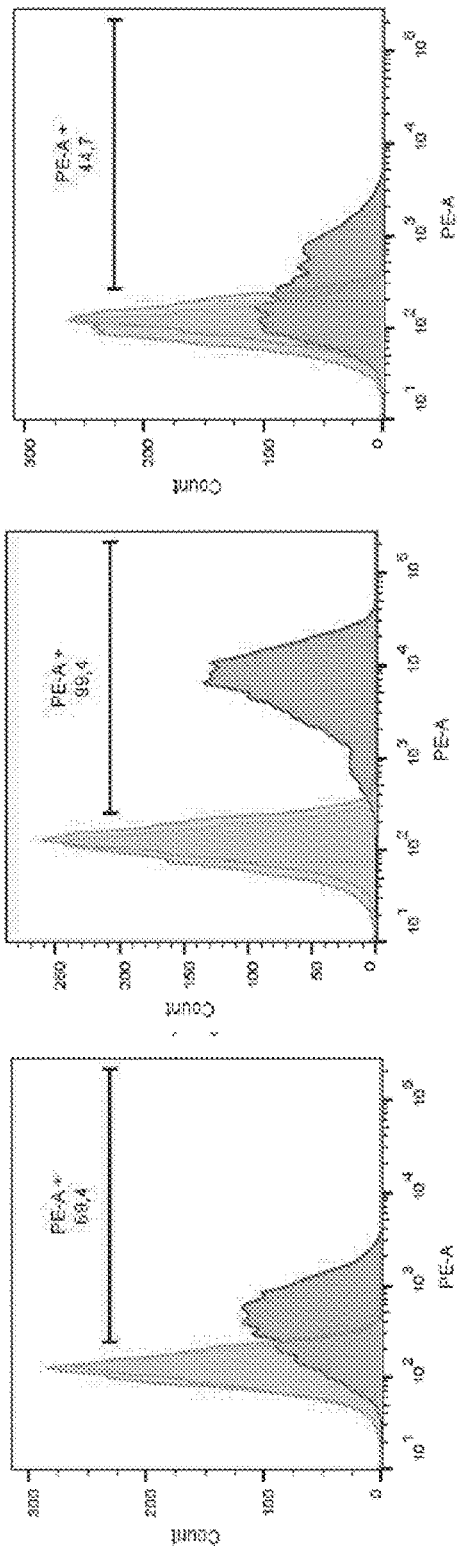
FIG. 9C

ANTI HLA-G SPECIFIC ANTIBODIES

CROSS-REFERENCE TO RELATED APPLICATIONS

This application is a continuation application of U.S. patent application Ser. No. 17/466,607, filed Sep. 3, 2021, now U.S. Pat. No. 11,312,774, which is a continuation application of U.S. patent application Ser. No. 17/080,017, filed Oct. 26, 2020, now U.S. Pat. No. 11,111,302, which is a continuation application of U.S. patent application Ser. No. 16/306,267, filed Nov. 30, 2018, which is a U.S. National Phase of International Patent Application No. PCT/EP2017/063503, filed Jun. 2, 2017, which claims priority to EP Patent Application No. 16305650.0, filed on Jun. 3, 2016, all of which are herein incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: INVE_001_04US_SeqList_ST25.txt, date recorded: Apr. 25, 2022, file size: ~45,367 bytes).

TECHNICAL FIELD

The present invention relates to antibodies, or antigen-binding fragments thereof, raised against an immunogenic peptide derived from the α3 domain of human leukocyte antigen G (HLA-G) protein.

TECHNICAL BACKGROUND

In cancer, one major immune escape mechanism is the expression of inhibitory molecules on the cell surface impairing T cell signaling. Many of these inhibitory molecules are considered as Immune Check Points (ICP) and refer to numerous inhibitory pathways first demonstrated to maintain self-tolerance and to modulate the duration and amplitude of physiological immune responses within peripheral tissues to avoid collateral tissue damages.

HLA-G was recently identified as an ICP molecule, which inhibits the effector functions of infiltrating immune cell subsets through the interaction with its specific receptors and is frequently upregulated in tumor cells (Carosella et al., 2015).

Furthermore, HLA-G can also be neo-expressed and/or up-regulated in pathological conditions such as viral infections, auto-immune and inflammatory diseases or after allotransplantation.

For instance, viruses such as HCMV (Human Cytomegalovirus), HSV-1 (Herpes Virus Simplex), RABV (Rabies Virus), HCV (hepatitis C Virus), IAV (Influenza A Virus) and HIV-1 (Human Immunodeficiency Virus type I) seem to up-regulate the expression of HLA-G to prevent infected cells from being recognized and attacked by CTL and NK cells. HLA-G can also control the CD8 T cell response against HIV-infected cells by directing CD8 cells to apoptosis and by affecting their cytotoxic properties (Tripathi and Agrawal, 2007).

HLA-G is a non-classical MHC class I molecule that was first identified in choriocarcinoma cells. MHC class I antigens comprise the classical antigens HLA-A, HLA-B and HLA-C, which exhibit three extracellular globular domains ($\alpha_1$, $\alpha_2$ and $\alpha_3$) associated with β2-microglobulin (β2M), as well as the non-classical antigens HLA-E, HLA-F and HLA-G.

Unlike classical MHC class I molecules, HLA-G is characterized by (i) a limited polymorphism, (ii) a tissue-restricted expression, and (iii) differs as well by its functions.

The eight exon gene coding for HLA-G molecules spans 4.4 kb on chromosome 6 (Geraghty et al., 1987; Ellis et al., 1990). Exons 2, 3 and 4 encode the $\alpha_1$, $\alpha_2$ and $\alpha_3$ extracellular domains, respectively. The primary RNA transcript can be alternatively spliced, resulting in the expression of seven isoforms, four of which are membrane-bound (HLA-G1, HLA-G2, HLA-G3 and HLA-G4), and three are soluble (HLA-G5, HLA-G6 and HLA-G7). HLA-G1 and HLA-G5 are the most prominent isoforms described, in part likely because of limited HLA-G reagents such as antibodies. Their structures are typical of classical HLA class I molecule: a heavy chain composed of three extracellular globular domains non-covalently associated to β2-Microglobulin (β2M) and a peptide, while the other isoforms are shorter, lacking one or two globular domains of the heavy chain, and without β2M association.

The immuno-inhibitory activity of HLA-G takes place through specific binding to three inhibitory receptors: leukocyte immunoglobulin-like receptor B1 (LILRB1/ILT2/CD85j), LILRB2 (ILT4/CD85d) and KIR2DL4 (or CD158d).

Through the interaction with these receptors, and opposite to classical MHC class I molecules, HLA-G acts as a down-regulator of the immune system's main functions, and neither stimulatory functions nor responses directed against allogenic HLA-G have been reported to date (Carosella et al., 2008a).

In a similar manner to other MHC class I molecules, LILRB receptors interact with the α3 domain of HLA-G. The LILRB1 receptor is expressed on B cells, some T cells, some NK cells and on all APCs (monocytes and dendritic cells), whereas LILRB2 expression is restricted to the myeloid lineage and only expressed on monocytes and dendritic cells.

LILRB1 and LILRB2 receptors bind a wide range of classical MHC molecules through the α3 domain/β2M complex or only the α3 domain respectively. Indeed, LILRB1 binds only β2M-associated HLA-G complexes, whereas LILRB2 recognizes both β2M-associated and β2M-free HLA-G molecules as well as truncated α1-α3 domain isoforms.

HLA-G is the ligand of highest affinity for LILRB2 receptor as compared to classical MHC class I molecules. The higher affinity of HLA-G for LILRB1 and LILRB2 receptors is particularly illustrated by the fact that HLA-G displayed at the surface of tumor cells is capable of engaging the LILRB1 and/or LILRB2 receptors even if classical MHC class I molecules are also expressed at their surface. This preferential interaction of HLA-G for LILRB receptors is sufficient to inhibit the cytolytic functions of immune effector cells.

LILRB1 and 2 receptors do not bind the same HLA-G forms and present a higher affinity for HLA-G multimers than monomeric structures (HoWangYin et al., 2012). This higher affinity of LIRB receptors for HLA-G was demonstrated to be related to the presence of aromatic amino acids Phe195 and Tyr197 within the α3 domain of HLA-G that are not present in classical MHC class I molecules.

The relevance of HLA-G expression as an escape mechanism employed by tumor cells to inhibit effector cells has been widely demonstrated (Loustau et al., 2013). Several approaches targeting HLA-G with the goal of mediating tumor cell rejection have been developed (Carosella et al., 2008b; Yan, 2011). Few anti-HLA-G antibodies have been generated, and only one blocking antibody is available (87G) (Blaschitz et al., 2000; Menier et al., 2003). This monoclonal antibody, 87G, interacts with the α1 domain of the heavy chain of HLA-G associated to β2M. Even though it has been described as capable of neutralizing HLA-G, and therefore restoring tumor rejection in vitro and in vivo (Agaugue et al., 2011), its applicability is compromised as HLA-G is frequently expressed as a β2M-free full length molecule or truncated isoforms. These various isoforms can also bind the LILRB2 inhibitory receptor.

HLA-G immunization has been remarkably difficult, yielding few specific antibodies. The reasons for this failure to generate neutralizing antibodies have been elucidated. In kidney-transplanted patients, it was demonstrated that the presence of HLA-G does not favor antibody production (Qiu et al., 2006). Recent in vitro studies have confirmed that HLA-G/LILRB1 interaction impairs B-cell maturation and antibody production in humans (Naji et al., 2014). HLA-G is also known to exert a tolerogenic function in mice, a species commonly used to generate monoclonal antibodies (Favier et al., 2001). HLA-G interacts with the PIR-B receptor, which is expressed in murine B-cells and which is functionally homologous to human LILRB1 and LILRB2 (Liang et al., 2002). HLA-G/PIR-B interaction would lead to B-cell inhibition thus preventing antibody production in mice.

A monoclonal antibody apparently directed to the α3 domain of classical MHC class I molecules, named TP25.99 has been developed (Tanabe et al., 1992). However, others have shown that it does not bind the α3 domain of HLA-G (Desai et al., 2000; Moy et al., 2000). This discrepancy could be explained by the hydrophobic characteristic of HLA-G α3 domain that is unfavorable to antibody generation.

While the international patent application WO2014/072534 proposes a method for generating and developing anti-HLA-G antibodies by DNA immunization with the complete α3 domain of HLA-G, there is still a need for anti-HLA-G antibodies which recognize all HLA-G isoforms and exhibit an improved specificity with respect to HLA-G.

SUMMARY OF THE INVENTION

The inventors have now succeeded in circumventing the difficulties for generating specific anti-HLA-G antibodies, by designing an immunogenic peptide from the α3 domain of HLA-G protein.

The first object of the invention is an isolated peptide consisting of sequence X1-THHPVFDYEATLR-X2 (SEQ ID NO: 49), wherein X1 is absent, Cysteine, Valine, or is a sequence selected from the group consisting of KTHV (SEQ ID NO: 50) or CKTHV (SEQ ID NO: 51), and X2 is absent or Cysteine.

Such a peptide is useful as an immunogen for producing antibodies specific for the α3 domain of HLA-G protein isoforms, preferably monoclonal antibodies.

A further object of the invention is an anti-HLA-G antibody, preferably a monoclonal antibody, which specifically recognizes the peptide as defined herein.

The antibody may be a full-length antibody, an antigen-binding fragment thereof, or a bispecific antibody.

A further object of the invention is a composition comprising such antibody and a pharmaceutically acceptable carrier.

Another subject of the invention is a nucleic acid comprising a nucleotide sequence encoding an antibody heavy chain variable region (VH), an antibody light chain variable region (VL) or both, of the antibody as defined herein.

A vector, preferably an expression vector, comprising said nucleic acid is also provided.

A host cell comprising the nucleic acid or the vector is further described.

Methods for producing anti-HLA-G antibodies are further provided. In a preferred embodiment is disclosed a method for producing an anti-HLA-G monoclonal antibody, comprising culturing the host cell comprising said nucleic acid or said vector under conditions allowing for expression of the antibody.

The antibody, nucleic acid or vector expressing said antibody, is particularly useful in treating a cancer or a viral infection.

A further subject of the invention is the use of the anti-HLA-G antibody described herein, in an in vitro diagnostic method for detecting or monitoring HLA-G in a biological sample.

Diagnostic kits comprising said antibody are further encompassed.

BRIEF DESCRIPTION OF THE DRAWINGS

FIG. 1A-FIG. 1C. Design of the immunogen, immunization and generation of anti-HLA-G antibodies. FIG. 1A. Amino acid sequence alignment of human HLA-G protein with HLA-E, A2, B7, B44, and CW3. The sequence alignment is provided for the three immunoglobulin domains of HLA-G: α1, α2, and α3. Residues highlighted in gray represent the differences with HLA-G. The regions in the α3 domain involved in LILRB1/2 binding are highlighted with black double-headed arrows. Amino acid sequence of the HLA-G specific PC-1 peptide is underlined and shown in bold. FIG. 1B. Generation of anti-HLA-G antibodies in immunized mice. Representative flow cytometric histograms of anti-HLA-G serum reactivity from an immunized BALB/c mouse (dark black lines/dark gray histograms) and from a non-immunized control mouse (light gray lines and histograms). Dashed lines denote the threshold above which signals are considered positive. Sera were prepared, diluted, and incubated with HLA-G5-coated beads and then incubated with a FITC-conjugated goat anti-mouse IgG secondary antibody. Fluorescence was analyzed by flow cytometry. Four dilutions of serum are shown. FIG. 1C. The reactivity of R4C-C3 (diamond symbols/dotted line) and R5C-D8 (circle symbols/dashed line) scFv antibodies to biotin-coupled PC1 peptide was assessed by ELISA. ScFv antibodies were serially diluted and tested by direct ELISA using biotin-PC1 coated on streptavidin microplates. Non-HLA-G biotinylated peptide was used as control (square and triangle symbols/thick lines).

FIG. 2A. Nucleotide and amino acid sequences of the κ light chain variable region of 15E7. The positions of "Complementary Determining Regions" (CDR1, CDR2 and CDR3), as well as those of "Framework Regions" (FR1, FR2, FR3 and FR4) of the antibody are displayed. FIG. 2B. Sequence alignment of the amino acid sequences of the κ light chain variable region of 15E7 and the corresponding mouse germinal amino acid gene. The amino acids in the sequence of 15E7 κ light chain which are different from the germline sequences are shown in bold. The positions of CDRs are indicated.

FIG. 3A. Nucleotide and amino acid sequences of the heavy chain variable region of 15E7. The positions of CDR1, CDR2 and CDR3 sequences, as well as those of FR of the antibody are displayed. FIG. 3B. Sequence alignment of the amino acid sequences of the heavy chain variable region of 15E7 and the corresponding mouse germinal amino acid gene. The amino acids in the sequence of 15E7 heavy chain which are different from the germline sequences are shown in bold. The positions of CDRs are indicated.

FIG. 4A. Nucleotide and amino acid sequences of the κ light chain variable region of the scFv R4C-C3. The positions of CDR1, CDR2 and CDR3 sequences, as well as those of FR of the scFv are displayed. FIG. 4B. Sequence alignment of the amino acid sequences of the κ light chain variable region of scFv R4C-C3 and the corresponding mouse germinal amino acid gene. The amino acids in the sequence of the scFv R4C-C3 κ light chain which are different from the germline sequences are shown in bold. The positions of CDRs are indicated.

FIG. 5A. Nucleotide and amino acid sequences of the heavy chain variable regions of the scFv antibody R4C-C3. The positions of CDR1, CDR2 and CDR3 sequences, as well as those of FR of the scFv antibody are displayed. FIG. 5B. Sequence alignment of the amino acid sequences of the heavy chain variable regions of scFv antibody R4C-C3 and the corresponding mouse germinal amino acid gene. The amino acids in the sequence of the scFv antibody R4C-C3 heavy chain that are different from the germline sequences are shown in bold. The positions of CDRs are displayed.

FIG. 9A-FIG. 9C. Flow cytometry analysis of surface HLA-G antigens on untreated or acid-treated K562-G1 and K562-PV cells (FIG. 9A, FIG. 9B) and JEG-3 cells (FIG. 9C). Surface HLA-G antigens were analyzed by following mAbs: MEM-G/9 (specific to native HLA-G complex), anti-hβ2M and 15E7. Histograms: light gray: Unstained; gray: isotype controls (IgM for the anti-β2M, IgG2a for the 15E7 mAb and IgG1 for the 4H84); dark gray; indicated antibody.

DETAILED DESCRIPTION OF THE INVENTION

Figure 6A:
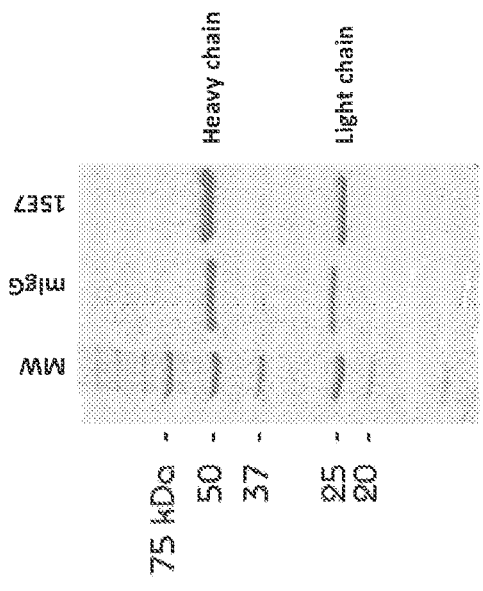
FIG. 6A. SDS-PAGE analysis of 15E7 monoclonal antibody. Lane 1: molecular weight markers—sequentially from top to down, 75 kDa, 50 kDa, 37 kDa, 25 kDa and 20 kDa. Lane 2: mouse IgG as control. Lane 3: 15E7 monoclonal antibody. Proteins were separated by SDS-PAGE and colored with Coomassie brilliant blue.

HLA-G therapeutic and diagnostic antibodies are lacking due to HLA-G tolerogenic functions on B cell maturation and antibody secretion. The inventors managed to bypass this inhibition by using a peptide derived from the HLA-G-α3 domain, which was able to induce anti-HLA-G specific antibodies.

The present invention provides anti-HLA-G monoclonal antibodies that bind specifically to HLA-G and which exhibit many desirable characteristics. Indeed, the anti-HLA-G antibodies generated strongly bind to either recombinant or endogenous HLA-G proteins in absence of cross-reactivity with classical MHC class I molecules.

The invention also relates to the use of such antibodies in order to restore the immune system resulting from pathological expression of HLA-G on the surface of some of the patient's cells. Accordingly, the antibodies are suitable for use in order to treat or alleviate a condition diagnosed in patients, when said condition takes advantage of the down-regulation of the immune system in a patient, due to the presence of HLA-G proteins. Antibodies of the invention may also be used for diagnostic or monitoring a condition in a patient.

Definitions

An antibody "specifically binds" to a target antigen if it binds with greater affinity, avidity, more readily, and/or with greater duration than it binds to other substances. "Specific binding" or "preferential binding" does not necessarily require (although it can include) exclusive binding. Generally, but not necessarily, reference to binding means preferential binding. The affinity of the binding is defined by association and dissociation rate constants, or $K_D$ (equilibrium dissociation). Typically, specifically binding when used with respect to an antibody refers to an antibody that specifically binds to ("recognizes") its target(s) with an affinity ($K_D$) value less than $10^{-8}$ M, e.g., less than $10^{-9}$ M or $10^{-10}$ M. A lower $K_D$ value represents a higher binding affinity (i.e., stronger binding) so that a $K_D$ value of $10^{-9}$M indicates a higher binding affinity than a $K_D$ value of $10^{-8}$M. Within the context of the present invention, "HLA-G protein binding" by antibodies or antigen-binding fragments of the invention means that the antibodies or antigen-binding fragments of the invention recognize HLA-G protein isoforms exhibiting α3 domain or found associated with an α3 domain, while being further found associated or not associated with β2-microglobulin protein or fragment thereof.

By "associated", it is meant a close (non-covalent) interaction between the considered domains or domains and proteins. Such an interaction can be achieved by the formation of hydrogen bonds, or van der Waals interactions, or ionic bonds.

By "specific binding" properties of the antibodies of the invention or antigen-binding fragments thereof it is meant that the antibodies or antigen-binding fragments thereof directly bind to the α3 domain of HLA-G protein to the exclusion of other domains of the HLA-G protein or to the exclusion of binding to other human proteins, in particular to the exclusion of binding to other HLA proteins. The binding capacity may be measured by determination of the binding affinity for the α3 domain of HLA-G protein, according to conventional tests known in the art of the invention, in particular the binding affinity can be assayed by ELISA, or Western Blot analysis. According to a specific embodiment, "specific binding" means that the interaction between the antibodies or antigen-binding fragments of the invention and the α3 domain of HLA-G protein through such a specific binding is more stable than interaction between the antibodies or antigen-binding fragments of the invention and other human proteins, or other HLA-G domains or other HLA proteins. Stability can be appreciated by comparing the persistence over time, or under competition conditions, of the antigen-antibody complex and, in particular, by measuring the dissociation constant of the antibodies recognizing the α3 domain of the HLA-G protein.

A "blocking antibody" is an antibody that inhibits the interaction of HLA-G proteins with any or all of its receptors, e.g. LILRB1 receptor and/or LILRB2 receptor. Therefore, by "blocking", it is typically meant that the biological function subsequent to binding between HLA-G proteins through an α3 domain and their receptors is abolished or strongly diminished in the presence of antibodies or antigen-binding fragments of the invention. The biological function referred to in this context is the immuno-inhibitory activity of HLA-G proteins exhibiting an α3 domain, as disclosed herein and assessed in the literature. Accordingly, it can be said that the antibodies or antigen-binding fragments are antagonist agents of HLA-G proteins, or antagonist agents of the effect(s) of HLA-G proteins having an α3 domain, because interfering with the activity of such HLA-G proteins and/or opposing to its activity at least in part or completely, directly or indirectly. Preferably the decrease in the interaction, i.e. binding, with any or all HLA-G receptors, is at least 20%, more preferably at least 30%, more preferably at least 40%, more preferably at least 50%, more preferably at least 60%, more preferably at least 70%, more preferably at least 80%, more preferably at least 90%, and most preferably 100%. Activity may be measured by binding assays known in the art.

The terms "Kabat numbering", "Kabat definitions and "Kabat labeling" are used interchangeably herein. These terms, which are recognized in the art, refer to a system of numbering amino acid residues that are more variable (i.e., hypervariable) than other amino acid residues in the heavy and light chain variable regions of an antibody, or an antigen binding portion thereof (Kabat et al. 1971; Kabat, et al. 1991).

As used herein, the term "CDR" refers to the Complementarity Determining Region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al, 1987 and Chothia et al., 1989) found that certain sub-portions within Kabat CDRs adopt nearly identical peptide backbone conformations, despite having great diversity at the level of amino acid sequence.

By "antigen-binding fragment" of an antibody of the invention, it is meant a part of an antibody, i.e. a molecule corresponding to a portion of the structure of the antibody of the invention that exhibits antigen-binding capacity for the α3 domain of HLA-G proteins. In a particular embodiment, said fragment exhibits substantially the same antigen-binding capacity for said domain as the antigen-binding capacity of the antibody having a full antibody structure. The antigen-binding capacity can be determined by measuring the affinity of the antibody and of the considered antigen-binding fragment to the targeted antigen.

Antigen-binding fragments of antibodies encompass fragments which comprise the hypervariable domains designated CDRs or part(s) thereof encompassing the recognition site for the immunogenic peptide. Each Light and Heavy chain (respectively VL and VH) of a four-chain immunoglobulin has three CDRs, designated VL-CDR1, VL-CDR2, VL-CDR3 and VH-CDR1, VH-CDR2, VH-CDR3, respectively. Thus the invention relates to fragments of antibodies of the invention (antigen-binding fragments), which comprise or consist in all or a selection of CDRs among VL-CDR1, VL-CDR2, VL-CDR3 and VH-CDR1, VH-CDR2 and VH-CDR3 or functional portions thereof, i.e. portions that exhibit the desired binding capacity, preferably with a high affinity, for the α3 domain of HLA-G proteins.

The term "monoclonal antibody" refers to an antibody that is derived from a single clone, including any eukaryotic, prokaryotic, or phage clone, and not the method by which it is produced. It is thus not limited to antibodies produced through hybridoma technology.

By "polyclonal serum" it is meant a serum comprising a heterogeneous population of many different antibodies or fragments thereof raised against a specific antigen, which are therefore specific for a number of distinct antigenic determinants found on said specific antigen.

As used herein, a "chimeric antibody" refers to an antibody in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, as long as they exhibit the desired biological activity As used herein, "humanized antibody" is a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from of an HVR of a non-human species (donor antibody) such as mouse, rat, rabbit or non-human primate having the desired specificity, affinity, and/or capacity for its targets. In some instances, residues of Complementarity-Determining Regions of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the framework regions (FR) are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and no more than 3 in the L chain. The humanized antibody optionally will also comprise at least a portion of an immunoglobulin constant region (Fc), typically that of a human immunoglobulin.

A "human antibody" is one that possesses an amino-acid sequence corresponding to that of an antibody produced by a human and/or has been made using any of the techniques for making human antibodies known in the art, including phage-display libraries. This definition of a human antibody specifically excludes a humanized antibody comprising non-human antigen-binding residues.

The "percent identity" of two amino acid sequences may be determined using the algorithm of Karlin and Altschul, 1990, as modified in Karlin and Altschul, 1993. Such an algorithm is incorporated into the NBLAST and XBLAST programs (version 2.0) of Altschul, et al. 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., 1997. When utilizing BLAST and Gapped BLAST programs, the default parameters of the respective programs (e.g., XBLAST and NBLAST) can be used.

"Conservative substitutions" will produce molecules having functional and chemical characteristics similar to those of the molecule from which such modifications are made. For example, a "conservative amino acid substitution" may involve a substitution of an amino acid residue with another residue such that there is little or no effect on the polarity or charge of the amino acid residue at that position. Desired amino acid substitutions (whether conservative or non-conservative) can be determined by those skilled in the art. For example, amino acid substitutions can be used to identify important residues of the molecule sequence, or to increase or decrease the affinity of the molecules described herein. Variants comprising one or more conservative amino acid substitutions can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The terms "subject," "individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

The term "treatment" or "treating" refers to an action, application or therapy, wherein a subject, including a human being, is subjected to medical aid with the purpose of improving the subject's condition, directly or indirectly. Particularly, the term refers to reducing incidence, or alleviating symptoms, eliminating recurrence, preventing recurrence, preventing incidence, improving symptoms, improving prognosis or combination thereof in some embodiments. The skilled artisan would understand that treatment does not necessarily result in the complete absence or removal of symptoms. For example, with respect to cancer, "treatment" or "treating" may refer to slowing neoplastic or malignant cell growth, proliferation, or metastasis, preventing or delaying the development of neoplastic or malignant cell growth, proliferation, or metastasis, or some combination thereof.

The Immunogenic Peptide

The inventors designed an immunogenic peptide to develop anti-HLA-G antibodies specific for HLA-G with no cross-reactivity toward classical MHC class I molecules.

HLA-G amino acid sequence differs from other MHC class I molecules (HLA-E, A2, B7, B44 and CW3) as shown in FIG. 1A. Variations in amino acids of the MHC class I sequences compare to the sequence of HLA-G are highlighted in gray, showing many hotspots within the different domains. Particularly, a highly specific sequence for HLA-G was identified within the α3 domain at position 194-197. This portion of HLA-G α3 domain encompasses amino acids essential for the interaction between HLA-G and its receptors (FIG. 1A).

On this basis, the inventors have designed an immunogenic peptide that consists of sequence X1-THHPVFD-YEATLR-X2 (SEQ ID NO: 49), wherein X1 is absent, Cysteine, Valine, or is a sequence selected from the group consisting of KTHV (SEQ ID NO: 50) or CKTHV (SEQ ID NO: 51), and X2 is absent or Cysteine.

In a preferred embodiment, the peptide is circular and consists of a sequence:

a. CTHHPVFDYEATLRC, (SEQ ID NO: 52)

b. CKTHVTHHPVFDYEATLRC, (SEQ ID NO: 53)

wherein a disulfide bond links the N-term and C-term Cysteine residues.

In another preferred embodiment, the peptide is linear and consists of a sequence selected from the group consisting of:

THHPVFDYEATLR; (SEQ ID NO: 54)

THHPVFDYEATLRC; (SEQ ID NO: 55)

VTHHPVFDYEATLRC; (SEQ ID NO: 56)

VTHHPVFDYEATLR; (SEQ ID NO: 57)

CTHHPVFDYEATLR; (SEQ ID NO: 58)

KTHVTHHPVFDYEATLR; (SEQ ID NO: 59)

KTHVTHHPVFDYEATLRC and (SEQ ID NO: 60)

CKTHVTHHPVFDYEATLR. (SEQ ID NO: 61)

The peptide may be produced by any technique known in the art, e.g. chemical synthesis or by recombination.

It is also provided a nucleic acid that encodes said peptide.

The invention also concerns a vector for the cloning and/or for the expression of the nucleic acid, especially a plasmid suitable for cloning and/or expressing in a host cell. According to a particular embodiment, regulation sequences for transcription and expression may be added.

The recombinant expression vectors typically contain a nucleic acid encoding the sequence to express, operably linked to a promoter, either constitutive or inducible. The vectors can be suitable for replication and integration in prokaryotes, eukaryotes, or both. Typical vectors contain transcription and translation terminators, initiation sequences, and promoters useful for regulation of the expression of the nucleic acid encoding said immunogenic peptide. The vectors optionally contain generic expression cassettes containing at least one independent terminator sequence, sequences permitting replication of the cassette in both eukaryotes and prokaryotes, i.e., shuttle vectors, and selection markers for both prokaryotic and eukaryotic systems.

As described in greater details below, the immunogenic peptide is useful for producing anti-HLA-G antibodies by immunization.

The Anti-HLA G Antibodies

The present invention relates to an antibody or an antigen-binding fragment thereof which specifically binds the immunogenic peptide defined above.

The anti-HLA-G antibodies of the invention all recognize the α3 domain of HLA-G proteins. In a specific embodiment, the antibody or antigen-binding fragment thereof specifically binds the α3 domain of HLA-G proteins having a conformation as naturally found in cells expressing HLA-G. In other words, such an antibody or antigen-binding fragment thereof of the invention recognizes a specific epitope of the α3 domain of HLA-G as naturally found in cells expressing HLA-G.

It is a purpose of the invention to produce specific anti-HLA-G antibodies for the HLA-G isoforms encompassing an α3 domain, or recognizing HLA-G isoforms associated with an α3 domain.

Accordingly, when referring to binding to a HLA-G protein, the invention especially relates to binding to a HLA-G isoform that exhibits an α3 domain.

In a particular embodiment, it is provided antibodies, or antigen-binding fragments thereof, which recognize the soluble forms of HLA-G.

In another embodiment, it is provided antibodies, or antigen-binding fragments thereof, which recognize the membrane-anchored forms of HLA-G.

In a most preferred embodiment, the antibodies of the present invention recognize the immunogenic peptide, either in linear form or in circular form, as well as HLA-G protein in soluble form and HLA-G protein at the cell surface (i.e. in natural conformation).

As mentioned above, HLA-G protein can be found under several structural (or three dimensional) forms, which are commonly called isoforms. HLA-G1 and HLA-G5 are respectively membrane-bound or secreted HLA-G proteins that are found associated or not with the β2-microglobulin protein. By contrast, HLA-G2, HLA-G3 and HLA-G4 are membrane-bound HLA-G protein isoforms not exhibiting concomitantly all of the α2 and α3 domains. HLA-G1 isoform can also be found as a dimeric form at the cell surface. HLA-G6 and HLA-G7 are secreted HLA-G protein isoforms also not exhibiting concomitantly all of the α2 and α3 domains.

Advantageously, the anti-HLA-G antibodies of the invention recognize all isoforms of HLA-G exhibiting an α3 domain.

In a preferred embodiment, an antibody or an antigen-binding fragment thereof of the invention binds at least one or several of the HLA-G protein isoforms selected amongst: HLA-G1, HLA-G2, HLA-G5 and HLA-G6 (monomeric and dimeric isoforms).

In a particular embodiment, the anti-HLA-G antibodies of the invention recognize HLA-G proteins, whether they are associated with the β2-microglobulin protein, or not.

The β2-microglobulin protein which, in some cases, can be found associated to HLA-G protein, is however not systematically present in all isoforms of the HLA-G protein. As detailed above, the presence of an associated β2-microglobulin protein is also not necessary to enable the binding of an HLA-G protein to the LILRB2 inhibitory receptor.

Within the context of the invention, "β2-microglobulin free HLA-G protein" therefore relates to HLA-G protein that is not associated with β2-microglobulin protein. By "β2-microglobulin free truncated HLA-G protein isoform" or "β2-microglobulin free truncated HLA-G protein isoform exhibiting an α3 domain", reference is made to an HLA-G protein not exhibiting all the domains that may be found in an HLA-G protein, and not associated with β2-microglobulin protein.

In a particular embodiment of the invention, the antibodies or antigen-binding fragments thereof specifically bind the α3 domain when present in HLA-G, in particular in β2-microglobulin free HLA-G, i.e., the β2-microglobulin free HLA-G exhibiting an α3 domain or the β2-microglobulin free truncated HLA-G exhibiting an α3 domain.

In a particular embodiment, it is provided antibodies, or antigen-binding fragments thereof, which bind the α3 domain of HLA-G protein when this protein is under a monomeric or dimeric form.

According to a particular embodiment, an antibody or an antigen-binding fragment thereof of the invention both binds the α3 domain of a HLA-G protein when said protein is under a monomeric and/or a dimeric form, and binds the α3 domain when present in a HLA-G protein, whether the β2-microglobulin protein is associated, or not associated.

For purposes of illustration of specific embodiments of the invention, antigen-binding fragments of an antibody that contains the variable domains comprising the CDRs of said antibody encompass Fv, dsFv, scFv, Fab, Fab', F(ab')2 which are well defined with reference to Kabat and also Roitt I. et al (Fundamental and Applied Immunology MEDSI/McGraw-Hill). Fv fragments consist of the VL and VH domains of an antibody associated together by hydrophobic interactions; in dsFv fragments, the VH:VL heterodimer is stabilized by a disulphide bond; in scFv fragments, the VL and VH domains are connected to one another via a flexible peptide linker thus forming a single-chain protein. Fab fragments are monomeric fragments obtainable by papain digestion of an antibody; they comprise the entire L chain, and a VH-CH1 fragment of the H chain, bound together through a disulfide bond. The F(ab')2 fragment can be produced by pepsin digestion of an antibody below the hinge disulfide; it comprises two Fab' fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen-binding sites, like the native immunoglobulin molecule; on the other hand, Fv (a VH-VL dimer constituting the variable part of Fab), dsFv, scFv, Fab, and Fab' fragments are monovalent, i.e. they comprise a single antigen-binding site.

In a most preferred embodiment, it is provided scFv fragments.

Fragments that comprise or consist in VH-CDR3 and/or VL-CDR3 or functional portions thereof are especially preferred when CDR3 regions appear to be determinant in antigen recognition specificity. Particular antigen-binding fragments comprise CDR1, CDR2 and CDR3 domains of a VH and/or a VL of an antibody.

These antigen-binding fragments of the invention can be combined together to obtain multivalent antigen-binding fragments, such as diabodies, tribodies or tetrabodies. These multivalent antigen-binding fragments are also part of the present invention.

Bispecific or multispecific antibodies are also encompassed, which are capable of simultaneously binding two different epitopes, on the same or on different antigens. Bispecific or multispecific antibodies can be obtained by different biochemical methods such as chemical conjugation of two antibodies, fusion of two antibody producing cell lines, or genetic approaches resulting in recombinant bispecific or multispecific antibody molecules.

In a particular embodiment of the invention, antibodies of the invention are monoclonal antibodies. The invention therefore also relates to monoclonal antibodies, meaning that a composition of these antibodies comprises antibodies that are identical, in terms of antigen-binding specificity and, accordingly, in terms of variable region composition.

In a further embodiment of the invention, antibodies or antigen-binding fragments thereof are provided as a polyclonal serum or are purified from a polyclonal serum.

According to the invention, the antibody may be a non-human mammalian antibody, e.g. a murine antibody, or a chimeric antibody. In a preferred embodiment, the antibody may be humanized. In a particular embodiment, human antibodies are encompassed.

In another embodiment, the invention also relates to a construct which comprises an antibody according to any of the definition provided herein or an antigen-binding fragment thereof, wherein said antibody or antigen-binding fragment thereof is conjugated with a functionally different molecule.

A construct of the invention may be either a fusion protein or a conjugate resulting from any suitable form of attachment including covalent attachment, grafting, chemical bonding with a chemical or biological group or a molecule, such as a protective group or a molecule suitable for protection against proteases cleavage in vivo, for improvement of stability and/or half-life of the antibody or antigen-binding fragment, with a biologically active molecule, especially a therapeutic active ingredient, e.g. a toxin or a cytotoxic agent, a vector (including especially a protein vector) suitable for targeting the antibody or antigen-binding fragment to specific cells or tissues of the human body, or with a label, e.g. a radioelement, or with a linker, especially when fragments of the antibody are used.

Examples of preferred antibodies, or antigen-binding fragments thereof, are described hereafter.

In a particular embodiment, it is provided an anti-HLA-G antibody which comprises:
  (a) a heavy chain variable region (VH), which comprises a heavy chain complementary determining region 1 (HC CDR1) of SEQ ID NO: 8, and/or a heavy chain complementary determining region 2 (HC CDR2) of SEQ ID NO: 10, and/or a heavy chain complementary determining region 3 (HC CDR3) of SEQ ID NO: 12; and/or
  (b) a light chain variable region (VL), which comprises a light chain complementary determining region 1 (LC CDR1) of SEQ ID NO: 2, and/or a light chain complementary determining region 2 (LC CDR2) of sequence KVS and/or a light chain complementary determining region 3 (LC CDR3) of SEQ ID NO: 5.

Preferably such antibody comprises:
  (a) a heavy chain variable region (VH), which comprises a heavy chain complementary determining region 1 (HC CDR1) of SEQ ID NO: 8, a heavy chain complementary determining region 2 (HC CDR2) of SEQ ID NO: 10, and a heavy chain complementary determining region 3 (HC CDR3) of SEQ ID NO: 12; and/or
  (b) a light chain variable region (VL), which comprises a light chain complementary determining region 1 (LC CDR1) of SEQ ID NO: 2, a light chain complementary determining region 2 (LC CDR2) of sequence KVS and a light chain complementary determining region 3 (LC CDR3) of SEQ ID NO: 5.

Still preferably such antibody may comprise:
  (a) a heavy chain variable region (VH) which comprises SEQ ID NO: 64 or a homologous sequence showing more than 80%, preferably more than 90%, still preferably more than 95% identity with SEQ ID NO: 64 and/or
  (b) a light chain variable region (VL), which comprises SEQ ID NO: 63 or a homologous sequence showing more than 80%, preferably more than 90%, still preferably more than 95% identity with SEQ ID NO: 63.

In a particular embodiment, the homologous sequence differs only by constitutive substitutions of amino acids.

In another embodiment, the homologous sequence is a humanized sequence.

In a particular aspect, the antibody is a full-length immunoglobulin G which comprises two heavy chains, including variable region (VH) comprising SEQ ID NO: 64; and two light chains, including variable region (VL), comprising SEQ ID NO: 63. Such antibody is named 15E7 and is described in greater details in the Experimental section.

In another particular embodiment, it is provided an antibody which comprises:
(a) a heavy chain variable region (VH), which comprises a heavy chain complementary determining region 1 (HC CDR1) of SEQ ID NO: 23, and/or a heavy chain complementary determining region 2 (HC CDR2) of SEQ ID NO: 25, and/or a heavy chain complementary determining region 3 (HC CDR3) of SEQ ID NO: 27; and/or
(b) a light chain variable region (VL), which comprises a light chain complementary determining region 1 (LC CDR1) of SEQ ID NO: 15, and/or a light chain complementary determining region 2 (LC CDR2) of sequence KVS, and/or a light chain complementary determining region 3 (LC CDR3) of SEQ ID NO: 18.

Preferably such antibody comprises:
(a) a heavy chain variable region (VH), which comprises a heavy chain complementary determining region 1 (HC CDR1) of SEQ ID NO: 23, a heavy chain complementary determining region 2 (HC CDR2) of SEQ ID NO: 25, and a heavy chain complementary determining region 3 (HC CDR3) of SEQ ID NO: 27; and/or
(b) a light chain variable region (VL), which comprises a light chain complementary determining region 1 (LC CDR1) of SEQ ID NO: 15, a light chain complementary determining region 2 (LC CDR2) of sequence KVS, and a light chain complementary determining region 3 (LC CDR3) of SEQ ID NO: 18.

Still preferably such antibody may comprise:
(a) a heavy chain variable region (VH) which comprises SEQ ID NO: 67 or a homologous sequence showing more than 80%, preferably more than 90%, still preferably more than 95% identity with SEQ ID NO: 67; and/or
(b) a light chain variable region (VL), which comprises SEQ ID NO: 65 or a homologous sequence showing more than 80%, preferably more than 90%, still preferably more than 95% identity with SEQ ID NO: 65.

In a particular embodiment, the homologous sequence differs only by constitutive substitutions of amino acids.

In another embodiment, the homologous sequence is a humanized sequence.

In a preferred aspect, it is provided a scFv which comprises a heavy chain variable region (VH) comprising SEQ ID NO: 67 and a light chain variable region (VL), comprising SEQ ID NO: 65. Such scFv fragment is named R4C-C3 and is described in greater details in the Experimental section.

In another particular embodiment, it is provided an antibody which comprises:
(a) a heavy chain variable region (VH), which comprises a heavy chain complementary determining region 1 (HC CDR1) of SEQ ID NO: 23, and/or a heavy chain complementary determining region 2 (HC CDR2) of SEQ ID NO: 25, and/or a heavy chain complementary determining region 3 (HC CDR3) of SEQ ID NO: 27; and/or
(b) a light chain variable region (VL), which comprises a light chain complementary determining region 1 (LC CDR1) of SEQ ID NO: 15, and/or a light chain complementary determining region 2 (LC CDR2) of sequence KVS, and/or a light chain complementary determining region 3 (LC CDR3) of SEQ ID NO: 20.

Preferably such antibody comprises:
(a) a heavy chain variable region (VH), which comprises a heavy chain complementary determining region 1 (HC CDR1) of SEQ ID NO: 23, a heavy chain complementary determining region 2 (HC CDR2) of SEQ ID NO: 25, and a heavy chain complementary determining region 3 (HC CDR3) of SEQ ID NO: 27; and/or
(b) a light chain variable region (VL), which comprises a light chain complementary determining region 1 (LC CDR1) of SEQ ID NO: 15, a light chain complementary determining region 2 (LC CDR2) of sequence KVS, and a light chain complementary determining region 3 (LC CDR3) of SEQ ID NO: 20.

Still preferably such antibody may comprise:
(a) a heavy chain variable region (VH) which comprises SEQ ID NO: 67 or a homologous sequence showing more than 80%, preferably more than 90%, still preferably more than 95% identity with SEQ ID NO: 67; and/or
(b) a light chain variable region (VL), which comprises SEQ ID NO: 66 or a homologous sequence showing more than 80%, preferably more than 90%, still preferably more than 95% identity with SEQ ID NO: 66.

In a particular embodiment, the homologous sequence differs only by constitutive substitutions of amino acids.

In another embodiment, the homologous sequence is a humanized sequence.

In another aspect, it is provided a scFv which comprises a heavy chain variable region (VH) comprising SEQ ID NO: 67 and a light chain variable region (VL), comprising SEQ ID NO: 66. Such scFv fragment is named R5C-D8.

The sequences of the variable regions of the antibodies are listed in the sequence listing, and described as follows.

```
VL κ chain of antibody 15E7:
                                          (SEQ ID NO: 1)
FR1: DVLMTQIPFSLPVSLGDQASISCRSS (SEQ ID NO: 2)
CDR1: QSIVHRSGNTY (SEQ ID NO: 3)
FR2: LEWYLQKPGQSPKLLIY

CDR2: KVS (SEQ ID NO: 4)
FR3: NRFSGVPDRFSGSGSGTDFTLKISRVEAEDLGVYYC (SEQ ID NO: 5)
CDR3: FQGSHLPPT (SEQ ID NO: 6)
FR4: FGGTTLEIK

VH chain of antibody 15E7:
                                          (SEQ ID NO: 7)
FR1: QVQLQQPGAELVRPGSSVKLSCKAS (SEQ ID NO: 8)
CDR1: GYTFTDYW
```

-continued

FR2: MDWVKQRPGQGLEWIGT (SEQ ID NO: 9)

CDR2: IYPSDSST (SEQ ID NO: 10)

FR3: HYNQEFKGKATMTVDKSSSTAYMHLSSLTSEDSAVYYC (SEQ ID NO: 11)

CDR3: AREGLAGVFYFDY (SEQ ID NO: 12)

FR4: WGQGTTLTVSS (SEQ ID NO: 13)

VL κ chain of scFv R4C-C3

FR1: DVLMTQTPLSLPVSLGDQASISCRSS (SEQ ID NO: 14)

CDR1: QSLVHSNGNTY (SEQ ID NO: 15)

FR2: LHWYLQKPGQSPKLLIY (SEQ ID NO: 16)

CDR2: KVS

FR3: NRFSGVPDRFSGSGSGTDFTLKISRVEAEDLGVYFC (SEQ ID NO: 17)

CDR3: SQSTHFPPT (SEQ ID NO: 18)

FR4: FGGGTKLEII (SEQ ID NO: 19)

VL κ chain of scFv R5C-D8

FR1: DVLMTQTPLSLPVSLGDQASISCRSS (SEQ ID NO: 14)

CDR1: QSLVHSNGNTY (SEQ ID NO: 15)

FR2: LHWYLQKPGQSPKLLIY (SEQ ID NO: 16)

CDR2: KVS

FR3: NRFSGVPDRFSGSGSGTDFTLKISRVEAEDLGVYFC (SEQ ID NO: 17)

CDR3: SQSTHVPPT (SEQ ID NO: 20)

FR4: FGAGTKLELK (SEQ ID NO: 21)

VH chain of scFv's R4C-C3 & R5C-D8

FR1: QVQLKQSGPQLVRPGASVKIPCKAS (SEQ ID NO: 22)

CDR1: GYSFTNYW (SEQ ID NO: 23)

FR2: MHWVKQRPGQGLEWIGM (SEQ ID NO: 24)

CDR2: IAPSDSDS (SEQ ID NO: 25)

FR3: RLNQNFKDKATLTVDKSSSTAYMQLSSPTSEDSAVYYC (SEQ ID NO: 26)

CDR3: AREGVTMITTGLDY (SEQ ID NO: 27)

FR4: WGQGTTLTVSS (SEQ ID NO: 28)

Additional antibodies (named N27F12 and N38F4) and scFv (named 3157-C57-R6B-C10, 3157-C57-R6B-G3 and 3157-C57-R6B-H10) have been produced. The sequences of the variable regions of said additional antibodies and scFv are listed in the sequence listing, and described as follows.

VL κ chain of antibody N27F12:

FR1: ENVLTQSPAIMAASLGEKVTMTCSAS (SEQ ID NO: 68)

CDR1: SSVSSNF (SEQ ID NO: 69)

FR2: LHWYQQKSGTSPKLWIY (SEQ ID NO: 70)

CDR2: GTS

FR3: NLASGVPARFSGSGTGISYSLTVSNMEAENDAAYYC (SEQ ID NO: 71)

CDR3: QQWNAYPFT (SEQ ID NO: 72)

FR4: FGAGTKLELK (SEQ ID NO: 21)

VH chain of antibody N27F12:

FR1: EVKLEESGGGLVQPGGSMKLSCVAS (SEQ ID NO: 73)

CDR1: GFTFSSYW (SEQ ID NO: 74)

FR2: LSWVRQSPEKGLEWVAE (SEQ ID NO: 75)

CDR2: VRLKSDNYAT (SEQ ID NO: 76)

FR3: SYAESVKGKFTISRDDANSRLYLQMNSLRPEDTGIYYC (SEQ ID NO: 77)

CDR3: TTGDY (SEQ ID NO: 78)

FR4: WGQGTTLTVSS (SEQ ID NO: 13)

VL κ chain of antibody N38F4:

FR1: DVVMTQIPLSLPVSLGDQASISCRSS (SEQ ID NO: 79)

CDR1: QSLVNSNGNTL (SEQ ID NO: 80)

FR2: LHWYLQKPGQSPKLLIY (SEQ ID NO: 16)

CDR2: KVS

FR3: NRFSGVPDRFSGSGSGTDFTLKISRVEAEDLGVYFC (SEQ ID NO: 17)

CDR3: SQSTHVPWT (SEQ ID NO: 81)

FR4: FGGGTKLEIK (SEQ ID NO: 82)

VH chain of antibody N38F4:

FR1: EVKLEESGGGLVQPGGSMKLSCVAS (SEQ ID NO: 73)

CDR1: GLTFSSYW (SEQ ID NO: 83)

FR2: MSWVRQSPEKGLEWVAE (SEQ ID NO: 84)

CDR2: IRLRSDNYVK (SEQ ID NO: 85)

FR3: QYADSVKGRFTISRDDSKGRLYLQMNRLRGDDTGIYFC (SEQ ID NO: 86)

CDR3: TTGDY (SEQ ID NO: 78)

FR4: WGQGTTLTVSS (SEQ ID NO: 13)

VL κ chain of scFv 3157-C57-R6B-C10 and 3157-C57-R6B-G3

FR1: DVLMTQTPLSLPVSLGDQASISCRSS (SEQ ID NO: 14)

CDR1: QTIVHSNGNTY (SEQ ID NO: 87)

FR2: LEWYLQKPGQSPKLLIY (SEQ ID NO: 3)

CDR2: KVS

FR3: NRFSGVPDRFSGSGSGTDFTLKISRVEAEDLGVYYC (SEQ ID NO: 4)

CDR3: FQGSHVPPT (SEQ ID NO: 88)

FR4: FGGGTKLEIK (SEQ ID NO: 82)

VH chain of scFv 3157-C57-R6B-C10

FR1: EVQLQQSGAELVKPGTSVKLSCKAS (SEQ ID NO: 89)

CDR1: GYTFTRNW (SEQ ID NO: 90)

FR2: ITWVRLRPGQGLEWIGD (SEQ ID NO: 91)

CDR2: IYPGDAST (SEQ ID NO: 92)

FR3: HYNGKFKNKATLTVDTSSSTAYLQVSSLTSEDSAVYYC (SEQ ID NO: 93)

CDR3: AREQVQFAMFFDV (SEQ ID NO: 94)

FR4: WGTGATVTVSS (SEQ ID NO: 95)

VH chain of scFv 3157-C57-R6B-G3

FR1: QVQLQQPRAELVKPGASVKMSCKAS (SEQ ID NO: 96)

CDR1: GYTFARYW (SEQ ID NO: 97)

FR2: ISWLKLRPGQGLEWIGD (SEQ ID NO: 98)

CDR2: IYPGDDST (SEQ ID NO: 99)

FR3: HYNGKFKNKATLTVDTSTSTAYIQLSSLTSEDSAVYYC (SEQ ID NO: 100)

CDR3: AREQVQFAMFFDV (SEQ ID NO: 94)

FR4: WGTGATVTVSS (SEQ ID NO: 95)

VL κ chain of scFv 3157-C57-R6B-H10

FR1: DVLMTQTPLSLPVSLGDQASISCRSS (SEQ ID NO: 14)

CDR1: QSIVHSNGNTY (SEQ ID NO: 101)

FR2: LEWYLQKPGQSPKLLIY (SEQ ID NO: 3)

CDR2: KVS

FR3: NRFSGVPDRFSGSGSGTDFTLKISRVEAEDLGVYYC (SEQ ID NO: 4)

CDR3: FQGSHVPPT (SEQ ID NO: 88)

FR4: FGGGTKLEIK (SEQ ID NO: 82)

VH chain of scFv 3157-C57-R6B-H10

FR1: QVQLQQPGAELVRPGSSVKLSCKAS (SEQ ID NO: 7)

CDR1: GYTFTDYW (SEQ ID NO: 8)

FR2: MDWVKQRPGQGLEWIGT (SEQ ID NO: 9)

CDR2: IYPSDSST (SEQ ID NO: 10)

FR3: HYNQEFKGKATMTVDKSSSTAYMHLGSLTSEDSAVYYC (SEQ ID NO: 102)

CDR3: AREGLAGVFYFDY (SEQ ID NO: 12)

FR4: WGQGTTLTVSS (SEQ ID NO: 13)

The present disclosure also provides antibody variants of the above preferred antibodies, with improved biological properties of the antibody, such as higher binding affinity. Amino acid sequence variants of the antibody can be prepared by introducing appropriate nucleotide changes into the antibody nucleic acid, or via peptide synthesis. Such modifications include, for example, deletions from, and/or insertions into and/or substitutions of, residues within the amino acid sequences of the antibody. Any combination of deletion, insertion, and substitution is made to achieve the final construct, provided that the final construct possesses the desired characteristics. Nucleic acid molecules encoding amino acid sequence variants of the antibody can be prepared by a variety of methods known in the art. These methods include, but are not limited to, oligonucleotide-mediated (or site-directed) mutagenesis, PCR mutagenesis, and cassette mutagenesis of an earlier prepared variant or a non-variant (natural) version of the antibody. In one embodiment, the equilibrium dissociation constant ($K_D$) value of the antibodies of the invention is less than $10^{-8}$ M, particularly less than $10^{-9}$ M or $10^{-10}$ M. The binding affinity may be determined using techniques known in the art, such as ELISA or biospecific interaction analysis, or other techniques known in the art.

Any of the antibodies described herein can be examined to determine their properties, such as antigen-binding activity, antigen-binding specificity, and biological functions, following routine methods.

Any of the antibodies described herein can be modified to contain additional non-proteinaceous moieties that are known in the art and readily available, e.g., by pegylation, glycosylation, and the like. Modifications that can enhance serum half-life are of interest.

Production of the Anti-HLA-G Antibodies by Immunization

In an aspect of the invention, the immunogenic peptide described above may be useful as an immunogen for producing antibodies specific for the α3 domain of a HLA-G protein.

For illustration purposes, the antibodies or fragments thereof of the invention may thus be obtained through immunization of a mammal, in particular a rodent, especially mice or rats, with an immunogenic peptide as described above. It can be concluded that various mammal genotypes are suitable for implementing the present invention through immunization of a mammal.

Immunization protocols may encompass priming and boosting steps, as described in greater details below.

The invention thus also relates to a method of production of an antibody or an antigen-binding fragment thereof according to the present invention, which comprises a. Administering to a non-human animal, the immunogenic peptide as described above, b. Recovering from sera or plasma samples obtained from the animals the elicited antibodies and checking their specificity for the α3 domain of HLA-G protein, and;

c. Optionally, cloning the recovered antibodies, and d. Optionally, preparing antigen-binding fragments from the recovered antibodies.

Administration, recovery of generated antibodies or antigen-binding fragments and subsequent cloning can be achieved through conventional methods in the art. Characterization methods prior to cloning using for example advanced sequencing methods are also well known in the art.

The preparation of antigen-binding fragments from the recovered antibodies can also be achieved through conventional methods in the art, in particular through high-throughput synthesis technologies.

Host animals for antibodies or antigen-binding fragments production can be mammals to the exclusion of the human, especially rodents, in particular mice.

According to a particular embodiment, the method of production disclosed herein also involves a step of sacrificing the host animals used for the production of the antibodies of the invention.

According to a particular embodiment, the method of production of an antibody or an antigen-binding fragment thereof according to the present invention encompasses the concomitant administration, in step a., of an adjuvant, the latter being defined as any ingredient, in particular compound, that acts to assist, accelerate, prolong or enhance antigen-specific immune responses when used in combination with administrated antigen(s) or immunogenic antigen fragment(s). Adjuvants are well known in the art of immunization (or vaccination) and immune-therapy.

According to a particular embodiment, administration according to step a. of the above-disclosed method is performed using a prime-boost immunization protocol implying a first administration (prime immunization or prime administration) of active immunogenic agents, and then at least one further administration (boost immunization or boost administration) that is separated in time from the first administration within the course of the immunization protocol. Boost immunizations encompass one, two, three or more administrations.

In a particular embodiment, the used prime-boost immunization protocol is either a homologous or a heterologous immunization protocol, meaning that the administered active, immunogenic, ingredients (e.g. antibodies or fragments) are respectively the same in the prime and boost administrations, or different.

In a particular embodiment, administration of active, immunogenic, ingredients in step a. of the above-mentioned method, including when a prime administration is performed and/or when a boost immunization is performed, is made concomitantly with an adjuvant, for example a Freund's adjuvant. Adjuvants are substances well known in the art.

In a specific embodiment, adjuvant administration is performed at both prime and boost immunizations, in particular when polypeptides or immunogenic fragments thereof are used for immunization.

Details of an immunization protocol that may be used as is or serve as a basis to design an immunization protocol aimed at producing antibodies or antigen-binding fragments thereof using immunization are given in the Example section below.

In another embodiment, the mammal is immunized with a nucleic acid or vector that encodes said immunogenic peptide, e.g. by means of DNA immunization.

Several delivery methods for DNA immunization are commonly available, such as intramuscular or intradermal injection of the nucleic acid or vector in saline solution, which delivers the DNA to the extracellular spaces. This method may be assisted by "electroporation", which uses electrical stimulation of biological tissues to transiently permeabilize cell(s) membrane(s). Alternatively, "gene-gun delivery" may be used, which involves bombarding the skin with plasmid-coated gold particles by employing ballistic devices, which enables DNA delivery directly into cell(s) cytoplasm. Alternatively, "needle free devices" may be used which rely on compressed to force the plasmid DNA into cells in the epidermis and dermis.

For polyclonal antibody preparation, serum is obtained from an immunized non-human animal and the antibodies present therein isolated by well-known techniques. The serum may be affinity purified using the immunogenic peptide set forth above linked to a solid support so as to obtain anti HLA-G antibodies.

In an alternate embodiment, lymphocytes from a non-immunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma, as described in Harlow et al., 1988; Hammerling, et al, 1981.

Alternatively, monoclonal antibodies of the invention, or fragments thereof, can be prepared using any other known techniques, including the use of recombinant, and phage display technologies, or a combination thereof.

Recombinant production of the monoclonal antibodies or fragments thereof involves expressing nucleic acids that encode the antibodies or fragments thereof in suitable host cells, as described below.

Recombinant Production of the Anti-HLA-G Antibodies

The invention also relates to a nucleic acid molecule encoding an antibody or an antigen-binding fragment thereof of the invention, as disclosed herein.

In particular it is provided a nucleic acid comprising a nucleotide sequence encoding an antibody heavy chain variable region (VH), an antibody light chain variable region (VL) or both, of the anti-HLA-G antibody as described above.

Nucleotide sequences of the CDRs herein described can be easily designed or sequenced.

For illustration purposes, the nucleotide sequences of the light and heavy chain variable regions of monoclonal antibody 15E7 are SEQ ID NO: 35 and SEQ ID NO: 38, shown in FIGS. 2A and 3A, respectively.

Nucleotide sequence of the light chain variable region of scFv R4C-C3 is SEQ ID NO: 41 shown in FIG. 4A while the R4C-C3 heavy chain nucleotide sequence, namely SEQ ID NO: 46, is shown in FIG. 5A.

It is further described a method for producing recombinant antibodies, or fragments thereof.

Nucleic acids encoding heavy and light chains of the antibodies of the invention are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence. Expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences.

In one example, both the heavy and light chain coding sequences are included in one expression vector. In another example, each of the heavy and light chains of the antibody is cloned into an individual vector. In the latter case, the expression vectors encoding the heavy and light chains can be co-transfected into one host cell for expression of both chains, which can be assembled to form intact antibodies either in vivo or in vitro. Alternatively, the expression vector encoding the heavy chain and that encoding the light chain can be introduced into different host cells for expression each of the heavy and light chains, which can then be purified and assembled to form intact antibodies in vitro.

The antibodies as described herein, or fragments thereof, may be produced in prokaryotic or eukaryotic expression systems, such as bacteria, yeast, filamentous fungi, insect, and mammalian cells. It is not necessary that the recombinant antibodies of the invention be glycosylated or expressed in eukaryotic cells; however, expression in mammalian cells is generally preferred. Examples of useful mammalian host cell lines are human embryonic kidney line (293 cells), baby hamster kidney cells (BHK cells), Chinese hamster ovary cells/- or +DHFR (CHO, CHO-S, CHO-DG44, Flp-in CHO cells), African green monkey kidney cells (VERO cells), and human liver cells (Hep G2 cells).

Mammalian tissue cell culture is preferred to express and produce the polypeptides because a number of suitable host cell lines capable of secreting intact immunoglobulins have been developed in the art, and include the CHO cell lines, various Cos cell lines, HeLa cells, preferably myeloma cell lines, or transformed B-cells or hybridomas.

Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papillomavirus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example, calcium phosphate treatment or electroporation may be used for other cellular hosts. (See generally Sambrook et al., Molecular Cloning: A Laboratory Manual (Cold Spring Harbor Press, 2nd ed., 1989). When heavy and light chains are cloned on separate expression vectors, the vectors are co-transfected to obtain expression and assembly of intact immunoglobulins.

Host cells are transformed or transfected with the vectors (for example, by chemical transfection or electroporation methods) and cultured in conventional nutrient media (or modified as appropriate) for inducing promoters, selecting transformants, or amplifying the genes encoding the desired sequences.

Once expressed, the antibodies of the present invention, or fragments thereof, can be further isolated or purified to obtain preparations that substantially homogeneous for further assays and applications. Standard protein purification methods known in the art can be used. For example, suitable purification procedures may include fractionation on immunoaffinity or ion-exchange columns, ethanol precipitation, high-performance liquid chromatography (HPLC), sodium dodecyl sulfate polyacrylamide gel electrophoresis (SDS-PAGE), ammonium sulfate precipitation, and gel filtration (see generally Scopes, Protein Purification, Springer-Verlag, N.Y., 1982). Substantially pure immunoglobulins of at least about 90 to 95% homogeneity are preferred, and 98 to 99% or more homogeneity most preferred, for pharmaceutical uses.

Phage Display Methods

Antibodies with the desired binding characteristics can also be produced using phage display libraries and screening.

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phages typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization. Finally, naive libraries can also be made synthetically by cloning non-rearranged V-gene segments from stem cells, and using PCR primers containing random sequence to encode the highly variable CDR3 regions and to accomplish rearrangement in vitro.

Therapeutic Uses

The anti HLA-G antibodies or antigen-binding fragments thereof, nucleic acids encoding such antibodies or fragments, or vectors expressing the same, are useful in treating pathologies such as cancer or carcinogenic diseases as well as related or associated diseases or conditions, when these pathologies are associated with a tumor escape mechanism involving HLA-G. More generally the anti-HLA-G antibodies or antigen-binding fragments thereof are useful in treating pathologies involving inappropriate expression of HLA-G proteins in a host.

More specifically, it is herein described a method for treating a cancer or a viral infection, which method comprises administering a composition comprising an anti-HLA-G antibody or an antigen-binding fragment thereof, nucleic acids encoding such antibodies or fragments, or vectors expressing the same, in a patient in need thereof.

The anti-HLA-G antibodies or antigen-binding fragments thereof may be used as the sole active ingredient, or in combination with another treatment method, such as chemotherapy treatment, radiotherapy treatment, or another immunotherapy treatment including therapeutic vaccination.

The anti-HLA-G antibodies described here, alone or combined with other therapies, are useful to counteract the immune escape mechanisms related to HLA-G and boost the overall antitumor effect and benefit cancer patients.

In a particular embodiment, the antibodies, or antigen-binding fragments thereof, of the invention, may be blocking antibodies. "Blocking antibodies", or "neutralizing antibodies", refer to antibodies which inhibit HLA-G binding to at least leukocyte immunoglobulin-like receptor B1 (LILRB1/ILT2/CD85j) or LILRB2 (ILT4/CD85d).

According to a particular embodiment, binding between at least one or several of the following HLA-G protein isoforms: HLA-G1, HLA-G2, HLA-G5 or HLA-G6 and their receptors recognized by the α3 domain is prevented.

In a specific embodiment, an antibody or an antigen-binding fragment thereof of the invention blocks the binding of a HLA-G protein exhibiting an α3 domain to at least one of LILRB1 or LILRB2 receptors, in particular blocks the binding of said HLA-G protein to both LILRB1 and LILRB2 receptors.

In another embodiment, the antibodies, or antigen-binding fragments thereof, of the invention, may be conjugated to a cytotoxic agent. In some aspects, such a construction (also named antibody-drug conjugate or ADC) further comprises at least one spacer or linker, which can be a peptide linker or a non-peptide linker. Such linkers may be cleavable or not cleavable. Several ways of linking the antibody to the cytotoxic agents are known to the skilled person. ADCs are typically produced by conjugating the cytotoxic agent to the antibody through the side chains of either surface-exposed lysines or free cysteines generated through reduction of interchain disulfide bonds.

The cytotoxic agent or cytotoxin can be any molecule known in the art that inhibits or prevents the function of cells and/or causes destruction of cells (cell death), and/or exerts anti-neoplastic/anti-proliferative effects. A number of classes of cytotoxic agents are known to have potential utility in ADC molecules. These include, but are not limited to, amanitins, auristatins, daunomycins, doxorubicins, duocarmycins, dolastatins, enediynes, lexitropsins, taxanes, puromycins, maytansinoids, vinca alkaloids, tubulysins and pyrrolobenzodiazepines. Toxins, including plant toxins and bacterial toxins, may be used as a cytotoxic agent, e.g. tetanus or diphtheria toxins, ricin, saponin, endotoxin A, etc.

In a particular embodiment, the antibodies, or antigen-binding fragments thereof, of the invention, may be conjugated to a radionucleide.

In still another embodiment, the antibodies, or antigen-binding fragments thereof, of the invention, may be engineered (e.g. modified or chimerized) so that they comprise a Fc region that promotes antibody-dependent cell-mediated toxicity (ADCC), or complement dependent cytotoxicity (CDC). Many Fc variants have already been described for that purpose, e.g. Lazar et al, 2006; Moore et al, 2010.

Such antibodies or conjugates are useful in treating cancer.

Cancer refers to any type of cancer, and may be preferably chosen from bladder cancer, kidney cancer, urogenital cancer and melanoma. Other non-limitative examples of cancer diseases or neoplastic conditions, are leukemia, basal cell carcinoma, breast cancer, malignant mesothelomia, actinic keratosis, clear cell renal carcinoma, retinoblastoma, spinous cell carcinoma, in situ carcinoma, colorectal cancer, ovarian carcinoma, cutaneous T cell lymphoma, endometrial adenocarcinoma, classical Hodgkin lymphoma, lung carcinoma, cutaneous B cell lymphoma, gastric cancer, ampullary cancer, biliary cancer, pancreatic ductal adenocarcinoma, esophageal squamous cell carcinoma, hydatidiform moles.

During viral infections, up regulation of HLA-G expression forms a part of the strategy used by some viruses to escape destruction by the immune system.

Non-limitative examples of viral infections which can be treated according to the present invention are HIV infection, rabies virus infection or hepatitis B or hepatitis C virus infection, as well as an infection by HCMV (Human Cytomegalovirus), HSV-1 (Herpes Virus Simplex), or IAV (Influenza A Virus).

In another aspect, the present invention provides a composition, e.g. a pharmaceutical composition, containing an antibody or fragment thereof, as defined herein, formulated together with a pharmaceutical carrier. As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. The route and/or mode of administration will vary depending upon the desired results.

The selected dosage level will depend upon a variety of factors including the route of administration, the age, sex, weight, condition, general health and prior medical history of the patient being treated, etc. For example, the antibody of the invention can be administered at a dosage of 0.2-20 mg/kg from 3 times/week to 1 time/month.

In another aspect, the medicament or vaccine is a composition comprising a nucleic acid encoding said antibody or fragment, or a vector containing said nucleic acid.

The vector may advantageously be a viral vector, e.g. selected from the group consisting of retroviral vectors, lentivirus vectors, adenovirus vectors, vaccinia virus vectors, pox virus vectors, measles virus vectors and adenovirus-associated vectors.

The nucleic acid, vector or composition can be administered directly or they can be packaged in liposomes or coated onto colloidal gold particles prior to administration. In a particular embodiment, the nucleic acid that encodes the antibody of the invention can be administered in a naked form.

For genetic immunization, the vaccine compositions are preferably administered intradermally, subcutaneously, intramuscularly, into the tumors or in any types of lymphoid organs by injection or by gas driven particle bombardment, and are delivered in an amount effective to stimulate an immune response in the host organism. In a preferred embodiment of the present invention, administration comprises an electroporation step, also designated herein by the term "electrotransfer", in addition to the injection step.

The nucleic acids may also be administered ex vivo to lymphoid or myeloid cells using liposomal transfection, particle bombardment or viral transduction (including co-cultivation techniques). The treated cells are then reintroduced back into the subject to be immunized.

In still another aspect, the immunogenic peptide, a nucleic acid encoding said peptide, or a vector expressing said peptide, is used for in vivo production of anti-HLA-G antibodies in a patient.

Diagnostic Methods and Kits

The invention also provides means suitable for in vitro detecting HLA-G proteins or monitoring or diagnosing a health status or a pathologic condition, as well as means for monitoring or diagnosing a health status or pathologic condition, involving in a patient susceptible of presenting such a status or condition.

In a particular embodiment, the condition is a cancer or a viral infection.

In particular, the invention relates to an in vitro method for detecting HLA-G protein in a sample and/or monitoring or diagnosing a health status or pathologic condition through the analysis of a sample previously obtained from a patient susceptible of presenting a specific health status or having a pathologic condition, said method comprising:
  a. Contacting the sample with antibodies or antigen-binding fragment thereof as disclosed herein, under conditions enabling the formation of immune complexes, and
  b. Detecting in vitro the resulting immune complexes formed between said antibodies or antigen-binding fragments thereof and HLA-G protein.

According to a particular embodiment, the present invention enables the in vitro detection of HLA-G protein in a sample, for example a sample previously obtained from a patient susceptible of being pregnant, or a sample obtained from a patient having undergone organ or tissue or cell transplantation(s). As a result, the monitoring of a health status can be performed, i.e. a physiological status that does not necessarily involve the presence of a pathologic condition. Subsequent diagnosis of the presence or absence of a pathologic condition can therefore also be performed.

When the sample has been previously obtained from a patient susceptible of presenting a pathologic condition, subsequent monitoring or diagnosis of such a pathologic condition may also be performed. In a particular embodiment, pathologic conditions referred to are those disclosed above.

The invention also relates to a kit for an in vitro assay or diagnostic method as disclosed above, said kit comprising:
  a. An antibody or antigen-binding fragment thereof as disclosed herein,
  b. Reagent(s) appropriate for the formation of immune complex(es) between the antibody of (a)., or antigen-binding fragment thereof and the sample to assay;
  c. Optionally, reagent(s) appropriate for detecting the formation of the immune complex(es) of step b.

The detection of HLA-G protein may be achieved by any technique known in the art, such as immunohistochemistry or detection in liquid-phase such as an ELISA assay. According to a particular embodiment, there is provided a kit comprising: (a) a support having an immobilized anti-HLA-G antibody bound thereto, wherein the anti-HLA-G antibody is an antibody of the invention; and (b) a mobile anti-HLA-G antibody (which binds to another epitope of the HLA G protein) having a reporter molecule bound thereto. The reporter molecule may be any molecule which is detectable in a quantitative or nearly quantitative manner. For example, a reporter molecule may be a colorimetric agent, a fluorometric agent, a radioisotope, or an enzymatic agent having a detectable end-point.

The method according to the invention may optionally comprise the step of measuring HLA-G by comparing the quantity of label detected in the biological sample with an HLA-G standard.

The method according to the invention involves a biological sample. Such a sample may be selected from, but is not limited to a tissue sample, e.g. a tumor tissue sample, a blood sample, a medium contacting a tissue sample, and a medium contacting a cell, for example when isolated cells are used, amniotic fluid, a medium contacting an embryo. The inventive method may be used to diagnose or detect an HLA-G indicative condition. In this embodiment, a control value for an HLA-G indicative condition can be compared with the quantity of HLA-G found in the sample. Certain conditions may be indicated if HLA-G is low or absent, while others may be indicated by increased levels of HLA-G. One skilled in the art could easily determine the indicative levels useful in diagnosing a condition. Such HLA-G indicative conditions may include, but are not limited to pre-eclampsia, increased risk of pre-eclampsia, adverse fetal outcome, increased risk of adverse fetal outcome, cancer, or increased risk of cancer development.

Soluble HLA-G (sHLA-G) has also been reported as a biomarker for embryo quality in human in vitro fertilization (IVF). In a particular embodiment, the antibodies of the invention are thus useful to monitor the presence of HLA-G protein in embryo culture supernatants (ES), in order to assess the likelihood of success of implantation in a context of an IVF.

The present invention, thus generally described above, will be understood more readily by reference to the following examples, which are provided by way of illustration and are not intended to be limiting of the instant invention.

Abbreviations

APC: Antigen Presenting Cell
ATCC: American Type Culture Collection
$\beta$2M: Beta-2-Microglobulin
BSA: Bovine Serum Albumin
CDR: Complementarity-Determining Regions
CFA: Complete Freund's Adjuvant
CTL: Cytotoxic T Lymphocytes
CTLA-4: Cytotoxic T-Lymphocyte-associated Antigen 4
DC: Dendritic Cell
DIC: diisopropylcarbodiimide
DNA: DeoxyriboNucleic Acid
DMEM: Dulbecco's Modified Eagle Medium
ELISA: Enzyme-Linked ImmunoSorbent Assay
EC: Effective Concentration
FACS: Fluorescence-Activated Cell Sorting
FCS: Fetal Calf Serum
FITC: Fluorescein IsoThioCyanate
FR: Framework Region
h: hour
HAT: Hypoxanthine-Aminopterin-Thymidine
HES: HydroxyEthyl Starch
HLA: Human Leukocyte Antigen
HPLC: Liquid Chromatography High Performance
HRP: HorseRadish Peroxidase
ICP: Immune Check Point
ID: IDentity
IFA: Incomplete Freund's Adjuvant
IgG: Immunoglobulin G
ILT-2: Immunoglobulin-Like Transcript 2
ILT-4: Immunoglobulin-Like Transcript 4
IMDM: Iscove's Modified Dulbecco's Media
IP: IntraPeritoneally
IPTG: Isopropyl $\beta$-D-1-thiogalactopyranoside
IV: IntraVenous
IVF: In Vitro Fertilization
KDa: Kilo Dalton KIR2DL4: Killer cell Immunoglobulin like Receptor 2 Ig Domains and Long cytoplasmic tail 4
KLH: Keyhole Limpet Hemocyanin
LILRB1: Leukocyte Immunoglobulin Like Receptor B1
LILRB2: Leukocyte Immunoglobulin Like Receptor B2
M: Molar
MEM: Minimal Essential Medium
MHC: Major Histocompatibility Complex
mL: milliLiters
NK: Natural Killer cell
nM: NanoMolar
OD: Optical Density
ON: Overnight
PAGE: PolyAcrylamide Gel Electrophoresis
PBS: Phosphate Buffered Saline
PC-1: Peptide Constrained-1
PCR: Polymerase Reaction Chain
PD-1: Programmed cell Death protein 1
PD-L1: Programmed cell Death Ligand 1
PE: PhycoErythrin
PIR-B: Paired Immunoglobulin-Like Receptor B
PS: Penicillin/Streptomycin
RNA: RiboNucleic Acid
RPM: Revolutions Per Minute
RT: Room Temperature
SB: Super Broth
scFv: single-chain Variable Fragment
SDS: Sodium Dodecyl Sulfate
Sec: Seconds
SEQ: SEQuence
sHLA-G: soluble HLA-G
TBS: Tris Buffered Saline
TMB: TetraMethylBenzidine
UV: Ultra Violet
V: Volume
VH: Variable Heavy chain
VL: Variable Light chain
µL: MicroLiters

EXAMPLES

Materials and Methods
Peptide Synthesis
The PC-1 peptide [VTHHPVFDYEATLRC (SEQ ID NO:56)] used to generate monoclonal antibodies was synthesized by Fmoc standard chemistry using DIC as an activator on a Syro from MultiSynTech and subsequently purified by reverse phase HPLC (RP-HPLC).
The PC1 peptide was analyzed by Liquid chromatography-Mass spectrometry (LCMS).
Preparation of the Immunogen
The PC1 peptide was coupled to KLH via the side chain C-terminal cysteine as follows: 5 mg of peptide were used for conjugation. KLH protein (77600, ThermoFisher, Paris, France), dissolved in PBS, was activated with the sulfo-MBS linker (22312, ThermoFisher, Paris, France). Free linker was removed by dialysis. Peptide dissolved in PBS was incubated with activated KLH. Free peptide was removed by dialysis. The PC-1-KLH complex was dissolved in PBS 1× (pH7.2) and stored at −20° C.
Mice Immunization
Two different mouse strains (C57BL/6J and BALB/cJ), purchased from Janvier laboratories (Le Genest-St-Isle, France) and bred at Pasteur Institute animal facility (Paris, France), were used for immunization. Mice were 7 weeks old upon the first immunogen injection. They were intraperitoneally (IP) immunized with an emulsion of 50 µg of PC-1 peptide conjugated to KLH mixed with Complete Freund's Adjuvant (CFA F5881; Sigma, Lyon, France) (v/v), followed 10 days after by 1 IP injection with 50 µg of PC-1-KLH mixed with Incomplete Freund's Adjuvant (IFA; F5506; Sigma, Lyon, France) and then 3 injections with 25 µg of the PC-1-KLH/IFA at day 20, 30 and 185 after the first injection.

The PC1-KLH/CFA or IFA emulsion was prepared by vortex for 30 minutes at RT in the dark. The antibody response was monitored in plasma, from blood obtained by retro-orbital bleeding of immunized mice, by flow cytometry (FACS) and ELISA analyses (as described below).
Generation of Hybridomas
Mice were boosted intravenously (IV) with the immunogen 3 days before euthanasia. Spleens were harvested and splenocytes were purified for subsequent fusions with the immortalized myeloma cell line sp2/0-Ag14 in order to obtain antibody-producing hybridomas. The fusions were performed using polyethylene glycol based standard protocol (Köhler, G., C. Milstein. Continuous cultures of fused cells secreting antibody of predefined specificity. Nature, 1975. 256(5517): p. 495-7). The resulting hybridomas were then cultured in a selective DMEM medium supplemented with L-Glutamine (4 mM), heat inactivated FCS (20%), HAT (Hypoxanthine-Aminopterin-Thymidine, 1×), HES (HydroxyEthyl Starch 130, 2%) and Penicillin/Streptomycin (1%). Hybridomas were allowed to grow for 7 to 14 days in the selection medium for colony formation and antibody production. The production of antibodies that specifically recognize the linear and circular PC-1 peptide was assessed by ELISA and flow cytometry analysis respectively. Positive hybridomas were cloned and grown in order to identify single-cell-derived clones secreting monoclonal antibodies of interest.
Phage Display Technology
Construction of the Anti-HLA-G Single-Chain Antibody Gene Library
Spleen of each animal was sampled after the last boost in order to isolate RNA using the Tri Reagent kit (Molecular Research Center Inc., Cincinnati, USA) according to the manufacturer's instructions. RNA was reverse transcribed by RT-PCR and the resulting cDNA was amplified by PCR using primers intended for the amplification of DNA encoding murine VH, VLκ and VLλ. PCR products were first cloned in the pGEM®-T easy vector (Promega, Madison, Wis.), according to the manufacturer's instructions, yielding to two antibody gene sub-libraries encoding either the heavy (VH) or the light (VLk+VLλ) chain.
Construction of the single-chain antibody (scFv) library was performed as follows: firstly, the VL (VLk and VLλ) PCR products were cloned into the phagemid vector pTH; Secondly, the VH PCR products were cloned into pTH containing the VLk or VLλ repertoire. The cloning site contains a (Gly$_4$Ser)$_3$ linker sequence flanked by the restriction enzyme sites for VH and VL cloning followed by a hexahistidine tag and a c-myc tag. Plasmids and phagemids were grown in E. coli XL1-Blue MRF' bacteria (Stratagene, Amsterdam, Netherlands). Transformed bacteria containing the scFv gene library were harvested and plasmids/phagemids from the library were isolated using the Nucleobond Plasmid Midi Kit (Macherey-Nagel; Düren, Germany) according to the manufacturer's instructions, then aliquoted and stored at −80° C.
The size of the final scFv library was constituted of $1.2 \times 10^7$ clones containing approximately 93% full-size inserts as determined by PCR. The bacteria library was then packaged as phages/scFv library using helper phages M13KO7. The phages/scFv were produced at 30° C. and 250 rpm for 16 h. Cells were pelleted by centrifugation and the supernatant containing the phages was precipitated using polyethylene glycol procedure. The precipitated phages were resuspended, filtered through a 0.45 µM filter and stored at 4° C. before phage titration.

Screening the Library

The screening of the phage/scFv library was performed using 1 µg/mL of biotinylated-PC1 peptide coated on streptavidin ELISA high capacity plates (15501, Piece). Five rounds of panning with increasing stringency (2, 4, 8 and 15 washes for each successive round of panning) were applied. Free HLA-G PC1 peptide (10 µg/mL in TBS-Tween 20 0.1%) was used as a competitor for Phages/scFv elution. For the recovery and amplification of the selected phages, an exponentially growing E. coli culture was infected with the eluted phage suspension after each round of panning. To assess the reactivity of the selected phages, a phage-ELISA using biotinylated HLA-G PC1 peptide as antigen was performed after each round of panning. After the first and second round of panning, the signal was at the same level as the background; the signal increased to threefold the background after the fourth round of panning. According to the phage display technology, such signal increase corresponds to enrichment in specific binders. The phagemid DNA was extracted from the library after the fifth round of panning. 96 clones were isolated and produced on deep well microtiter plate (Maxisorp, Nunc, Danemark). Supernatants, containing phage particles, were tested by phage-ELISA method and 6 PC1-specific binders were identified (R4C-C3, R4C-B1, R4C-F2, R4C-F1, R4C-F12 and R5C-D8) and sequenced.

scFv Production

For protein expression, phagemid DNA isolated from the identified positive binders were transformed into the non-suppressor E. coli strain HB2151. Single colonies randomly chosen from the selected plates were inoculated into 5 mL of SB medium (Super Broth) supplemented with carbenicillin and glucose (1%). The cultures were incubated overnight under agitation at 37° C., and then transferred to a larger-scale SB cultures (500 µL of culture were transferred to 500 mL of fresh SB medium). Expression of the target proteins was induced by adding 1 mM IPTG (Isopropyl β-D-1-thiogalactopyranoside) when the cultures reached an $OD_{600}$ of 1. Cells were grown overnight (ON) at 16° C., and then harvested by centrifugation. The scFvs were extracted and purified using a nickel column (Ni-NTA spin column, Qiagen, Valencia, Calif.) according to the manufacturer's instructions.

Flow Cytometry Analysis

Cell Lines

K562 cells are human leukemia cells purchased from ATCC (American Type Culture Collection CCL-243). K562-G1 and K562-PV were obtained by nucleofection of K562 wild-type cells with either a HLA-G1 encoding vector or the corresponding mock vector, respectively. These cell lines were cultured in IMDM medium supplemented with 10% heat-inactivated FCS and 1% Penicillin/Streptomycin.

The lymphoblastoid cell lines, LCL-DES, LCL-BRO and RPMI8866, expressing classical MHC Class I molecules but not HLA-G were kindly gifted by D. Wiels (Institut Gustave Roussy, Villejuif, France). These cells were cultured in RPMI 1640 medium supplemented with 10% heat-inactivated FCS, 1% penicillin/streptomycin, 10 mM sodium pyruvate and 200 g/L D-glucose.

Bioplex Beads, Receptors and Monoclonal Antibodies

Bioplex beads (MC10028-01 and MC10062-01) were purchased from Bio-Rad (Marnes-la-Coquette, France), and PE-conjugated mouse IgG1 (Clone P.3.6.8.2.1. 12-4714) from eBiosciences (Paris; France), and FITC-conjugated rat IgG2a from BD Biosciences (clone: R35-95 553929, Le Pont de Claix; France).

HLA-G6 and HLA-G5 Protein Production

Coding sequences for α1α3 domains of HLA-G6 and α1α2α3 domains of HLA-G5 genes were cloned in pAcGP67 baculovirus transfer vector. Genetic constructions and plasmid amplifications of the pAcGP67 baculovirus vectors containing the different inserts were produced by Genecust (Luxembourg). Plasmids were amplified in DH5 bacteria hosts in Proteople facility at Institut Pasteur (Paris, France). Transfer vectors and AcMNPV linearized DNA (BaculoGold™ from BD) were co-transfected into *Spodoptera frugiperda* (Sf9) cells allowing recombination between homologous sites, transferring the inserts from the transfer vector to the AcMNPV DNA. Recombinant viruses coding for each protein were produced and used to infect Sf9 cells producing then the recombinant proteins.

Once recombinant proteins were expressed, cells were lysed and the lysate was added to an immobilized StrepTactin affinity resin column. After several wash steps to remove non-specifically bound proteins, bound StrepTag proteins were eluted with 2.5 mM desthiobiotin. Purified eluted proteins were analyzed by SDS-PAGE to validate the presence of HLA-G5, and were then aliquoted and stored at −20° C.

Coupling of Bioplex Beads

Bioplex beads were coated with the recombinant HLA-G5, HLA-G6 proteins or with the synthetic circular cPC-1 peptide (CTHHPVFDYEATLRC, SEQ ID NO: 52) following standard amine coupling chemistry procedure using the kit provided by Bio-Rad (Marnes-la-Coquette; France) according to supplier's instructions. As specificity (negative) controls, uncoupled beads or beads coated with a mutated peptide CTHHPVADAEATLRC (SEQ ID NO: 62) were used respectively. The circular cPC-1 peptide was designed to mimic the conformational structure of VTHHPVFD-YEATLRC (SEQ ID NO: 56) amino acids region at positions 189-203 within the α3 domain of HLA-G determined by previous crystallography studies (Clements et al., 2005). Conformational mimicry was obtained by replacing the N-terminal Valine residue of the PC-1 peptide with a Cysteine residue resulting in the formation of a disulfide bond between the N- and C-terminal Cysteine residues.

Analysis of Anti-HLA-G Sera and Monoclonal Antibodies

Detection of specific anti-HLA-G antibodies in sera of immunized mice or in supernatants of clonogenic hybridomas cell culture was assessed by flow cytometry. Flow cytometry was carried out first using HLA-G5, HLA-G6 and cPC-1 peptide coated beads.

Beads were incubated with different dilutions of sera or cell culture supernatants containing monoclonal antibodies for 1 h at RT, then washed twice and incubated for 30 min at RT with PE-conjugated goat anti-mouse IgG antibody (405307, Biolegend, USA). Flow cytometry analyses were performed using LSR FORTESSA (Beckton Dickinson, Le Pont-de-Claix, France); data were analyzed with FlowJo X software (Tree star, Ashland, USA). To determine the percentage of positive stained beads, electronic gates were set to exclude 99% of the fluorescent beads with the isotype control. Thus, positive stained beads were defined as those with staining intensity higher than those exhibited by 99% of the isotype control.

ELISA Assay 96-well microplates were coated with the PC-1 peptide at 1 µg/mL in PBS (100 µL/well), incubated overnight at RT and then blocked with 150 µL/well of PBS-dried skimmed milk for 1 h at RT. After one wash with PBS tween 0.05%, dilutions of sera or monoclonal antibodies were added (50 µL/well) for 2 h at RT. Plates were washed three times and peroxidase (HRP) conjugated goat anti-Mouse IgG was added at 1/10000 in PBS-tween 0.05%, 1% BSA (50 µL/well) for 1 h at RT. After three washes, plates were stained with TMB substrate (KPL, Gaithersburg, USA) and read at $OD_{450}$.

For phage display, HLA-G PC1 free peptide or coupled to BSA were coated onto 96-well microtiter plates (Maxisorp, Nunc, Danemark). Detection was assessed using an anti-histidine tag antibody (Qiagen, Courtaboeuf, France).

Additional Characterization of the Monoclonal Antibody 15E7

Isotyping

The 15E7 isotype was determined by ELISA assay using the Clonotyping Southern kit, (Clinisciences, Nanterre, France) according to the manufacturer's instructions. Briefly, plates were coated with a capture antibody (specific for each isotype) overnight at 4° C., and then washed twice with PBS 0.05% Tween. Plates were then allowed to warm at RT and the hybridoma supernatant containing the 15E7 monoclonal antibody was added for 1 h at RT. HRP-conjugated anti-isotype secondary antibodies, provided in the kit, were used at 1/2000. Plates were stained with TMB substrate (Eurobio/KPL, Gaithersburg, USA) and read at $OD_{450}$.

Production of the 15E7 Monoclonal Antibody

The 15E7 hybridoma was grown in vivo as ascites in mice. After sufficient growth to produce the desired monoclonal antibody, ascites fluids containing the monoclonal antibody were purified. Purification was achieved by chromatography using a standard protein A-sepharose column. Elution fractions containing the 15E7 were pooled, dialyzed, and concentrated as needed. Concentration was determined at $OD_{280}$ with an UV scan and adjusted at 2 mg/mL.

Determination of the Binding Affinity (BLITZ Technology)

Binding affinity and binding kinetics were determined by the BLITZ technology. The 15E7 monoclonal antibody was covalently linked to a biosensors chip AR2G (Pall ForteBio) via primary amines using standard amine coupling chemistry. Binding was measured by incubating the chip coupled to 15E7 with different concentrations of the PC-1 peptide coupled to BSA. The antigen-antibody association kinetics was followed for 120 seconds and the dissociation kinetics was followed for 100 seconds. The association and dissociation curves fit to 1:1.

Example 1: Production of Anti-HLA-G Antibodies in Mice

Design of the Immunogen

The inventors designed a highly HLA-G specific peptide corresponding to the α3 amino acid region 189-203 of HLA-G, referenced as "Peptide Constrained: PC-1" (FIG. 1A; in bold and underlined), and used it to immunize mice.

PC-1 sequence: VTHHPVFDYEATLRC (SEQ ID NO: 56)

PC-1 immunogen is expected to generate therapy-suitable anti-HLA-G monoclonal antibodies specific for HLA-G α3-containing isoforms independently of β2M association.

Immunization, Hybridoma Generation and scFv Production

The immunization protocol using the PC-1 peptide coupled to KLH is described in Materials and Methods section. C57BL/6 and BALB/c mice were used for peptide immunization.

Briefly, mice were intraperitoneally primed with PC-1-KLH conjugate in CFA and boosted with 4 IP in IFA. Sera from immunized mice were collected at different time points along the immunization procedure and were tested using Bioplex-HLA-G5, HLA-G6 and cPC-1 coupled beads. For each experiment, positive and negative controls were set up to determine the specific affinity of polyclonal antibodies obtained. Sera were considered positive if HLA-G-peptide beads showed a peak shift in FACS in comparison to those labelled with sera from non-immunized mice. When BALB/c and C57BL/6 mice were immunized with PC-1-KLH peptide, significant levels of anti-HLA-G IgG antibodies were detected in sera after each IP boost. FIG. 1B shows the staining of HLA-G5-coated beads obtained in the presence of serum collected from an immunized Balb/c mouse and a non-vaccinated control mouse. Anti-HLA-G antibodies were significantly detected in a dose-dependent manner even at the lowest doses of serum (dilution 1/1000). No specific binding was detected using control uncoupled beads (data not shown).

Mice with the highest anti-HLA-G antibody titers were used for hybridoma generation or for phage display.

Fusions were done as described in Materials and Methods section. ELISA positive hybridomas were subsequently cloned and confirmed again by ELISA to detect the clones of interest producing anti-HLA-G monoclonal antibodies.

Phage display process was carried out as detailed in Material and Methods. The reactivity of scFv clones R4C-C3, R4C-B1, R4C-F2, R4C-F1 and R5C-D8 to HLA-G peptides was assessed by ELISA. The R4C-C3 and R5C-D8 clones showed a high reactivity to Biotin-coupled PC1 peptide (FIG. 1C). R4C-C3 reacted with HLAG protein isoforms.

The hybridoma clone 15E7 and the scFv clones R4C-C3 were selected for further analysis.

Example 2: Genetic Characterization of the Mouse Monoclonal Antibody 15E7 and scFv R4C-C3

The cDNA sequences encoding the light and heavy chain variable regions of the monoclonal antibody 15E7 and the R4C-C3 scFv were obtained using standard PCR and DNA sequencing methods.

Monoclonal Antibody 15E7

The nucleotide and amino acid sequences of the light chain variable region of 15E7 are shown in FIG. 2A.

The nucleotide and amino acid sequences of the heavy chain variable region of 15E7 are shown in FIG. 3A.

The greatest variability in the light and heavy chains is located mainly within the hypervariable regions called Complementarity-Determining Regions (CDRs) which define the specificity of the antibody. Analysis of the 15E7 VL and VH sequences led to the CDR1, CDR2 and CDR3 regions delineation of the light and heavy chains respectively as shown in FIGS. 2A and 3A.

The sequence of the 15E7 κ light chain was compared to the known mouse germline immunoglobulin light chain sequences (FIG. 2B). The 15E7 light chain utilizes a VL segment from mouse germline IGKV1-117 and a JK segment from mouse germline IGKJ1.

The comparison of the 15E7 heavy chain (γ) sequence to the known mouse germline immunoglobulin heavy chain sequences demonstrated that the 15E7 heavy chain utilizes a VH segment from mouse germline IGHV1-61, a JH segment from mouse germline IGHJ2 and a DH segment from mouse germline IGHD4-1 (FIG. 3B).

These amino acid sequence comparisons highlight the strong homology of the heavy (93.1%) and the light (94.6%) chain sequences of 15E7 with the corresponding mouse germlines. Variations in the sequence of the light chain are distributed throughout FR1 and FR4, as well as in CDR1 and CDR3 regions (FIG. 2B), while variations in the sequence of the heavy chain are mostly confined to CDR regions and FR3 (FIG. 3B). Thus, these results demonstrate that the 15E7 monoclonal antibody is a mouse IgG that has undergone an affinity maturation process and has acquired a strong specificity/affinity for a specific HLA-G epitope.

The scFv clone R4C-C3

The nucleotide and amino acid sequences of the light chain variable regions of the scFv R4C-C3 is shown in FIG. 4A.

The R4C-C3 heavy chain nucleotide and amino acid sequences as shown in FIG. 5A. The VL and VH sequences of scFv R4C-C3 were analyzed and the CDRs regions of the light and heavy chains were delineated as depicted in FIGS. 4A and 5A.

The sequences of the scFv R4C-C3 κ light chains were compared to the known mouse germline immunoglobulin light chain sequences. This alignment demonstrated that the scFv R4C-C3 light chain utilizes a VL segment from mouse germline IGKV1-110 and a JK segment from mouse germline IGKJ1. The sequence alignments between scFv R4C-C3 and its corresponding mouse germline segments are shown in FIGS. 4B and 5B.

The comparison of the scFv heavy chain (γ) sequence to the known mouse germline immunoglobulin heavy chain sequences demonstrated that this chain utilizes a VH segment from mouse germline IGHV1S126, a JH segment from mouse germline IGHJ2 and a DH segment from mouse germline IGHD2-12. The sequence alignment between scFv R4C-C3 VH and the corresponding mouse germlines are shown in FIG. 5B. These amino acid alignments revealed that the sequences of light and the heavy chains of scFv R4C-C3 are 96.4% and 82.8% homologous to the germlines sequences. Variations in the light chain sequences are mainly located in the CDR3 regions (FIG. 4B), while variations in the heavy chain sequence are distributed throughout FR1, FR2, FR3 and all CDRs (FIG. 5B). The high mutation rate in the sequence of the heavy chain proves that scFv R4C-C3 has undergone an affinity maturation process and acquired a strong affinity for the HLA-G derived peptide.

Example 3: Characterization of Anti-HLA-G Monoclonal Antibody 15E7

Protein Analysis

The 15E7 monoclonal antibody was analyzed by SDS-PAGE gel electrophoresis (FIG. 6A). The heavy chain molecular weight is around 50 kDa and light chain around 25 kDa. Having two copies of each, the molecular weight of 15E7 is estimated to 150 kDa confirming that the monoclonal antibody 15E7 belongs to the murine IgG 2a class.

Isotyping and Affinity Determination

The isotype of 15E7 was assessed by ELISA. 15E7 isotype was determined to be IgG2a.

Figure 6B:
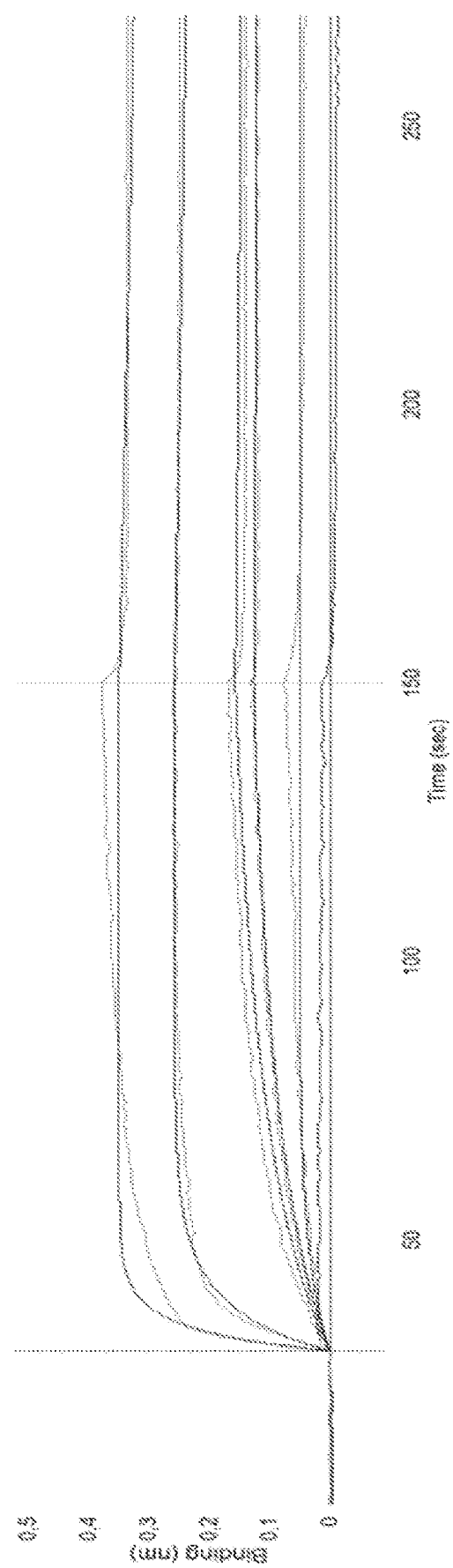
FIG. 6B. Kinetic analysis of the binding of the 15E7 monoclonal antibody to the PC-1 peptide using the Blitz biolayer interferometry system. The 15E7 monoclonal antibody was immobilized to AR2G chips by amino coupling. Various concentrations of PC-1 peptide/BSA (from 5 to 600 nM) were incubated with 15E7 coupled to the biosensor surface. Analysis started at time point 30 seconds for a duration of 120 seconds (association phase) after which only buffer was incubated for 100 seconds to record the dissociation of PC-1/BSA from 15E7. Left side of the dotted line (at 150 seconds) shows the association kinetics, whereas the right side indicates the dissociation phase. The upper line corresponds to the binding of 15E7 to the highest concentration of peptide (600 nM) and the lower line to the lowest concentration of peptide (5 nM). The binding was proportional to the peptide concentration (intermediate lines).

The affinity of 15E7 was assessed by the BLITZ technology as described in the Materials and Methods section. Representative data are shown in FIG. 6B. Various concentrations of the PC-1 peptide conjugated to BSA ranging from 5 to 600 nM were incubated with the 15E7 coupled to the biosensor chip. For each concentration, the association ($k_a$) and dissociation ($k_d$) rates were measured and used to calculate the affinity constant $K_D$ ($k_a/k_d$), evaluated here as 1.57 nM.

Specificity to HLA-G Proteins and Peptides

In order to determine the reactivity of 15E7 with the HLA-G5 and G6 protein and cPC-1 peptide, a flow cytometry based titration was performed.

Figure 7B:
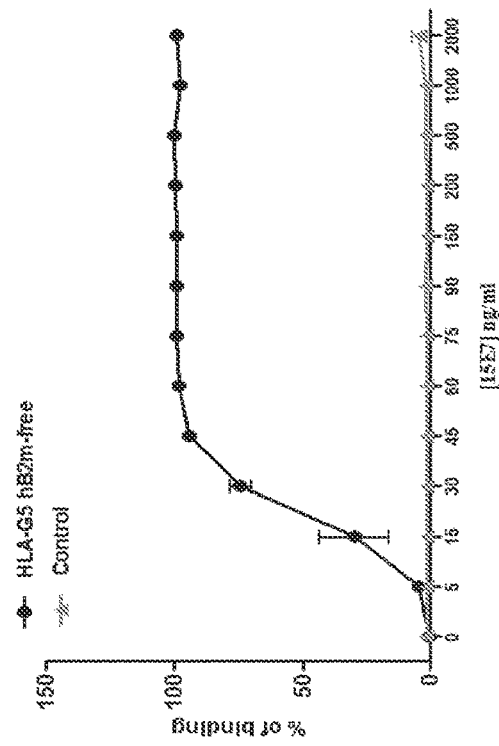
FIG. 7A-FIG. 7C. Dose dependent binding of the monoclonal antibody 15E7 to its targets: cPC-1 peptide (FIG. 7A); HLA-G5 recombinant protein (FIG. 7B) or HLA-G6 recombinant protein (both proteins without β2M association) (FIG. 7C). Various serial concentrations of 15E7 were used to determine a dose-dependent binding activity. The binding detection was carried out by flow cytometry using a PE-conjugated goat anti-mouse antibody. Binding is represented as a percentage of positive labeled beads with 15E7 compare to the staining with the isotype control (IgG2a). $EC_{50}$ of 15E7 was evaluated at 2 ng/mL on cPC-1 peptide, at 28 ng/mL on HLA-G5 and at 120 ng/mL on HLA-G6 proteins. Measurements were performed in triplicate (n=3); error bars indicate SD. Dark lines represent the binding of 15E7 to ligands coated beads while gray lines represent the binding of 15E7 to control beads [beads coated with a mutated peptide (FIG. 7A) or uncoupled beads (FIG. 7B and FIG. 7C)].
Figure 7A:
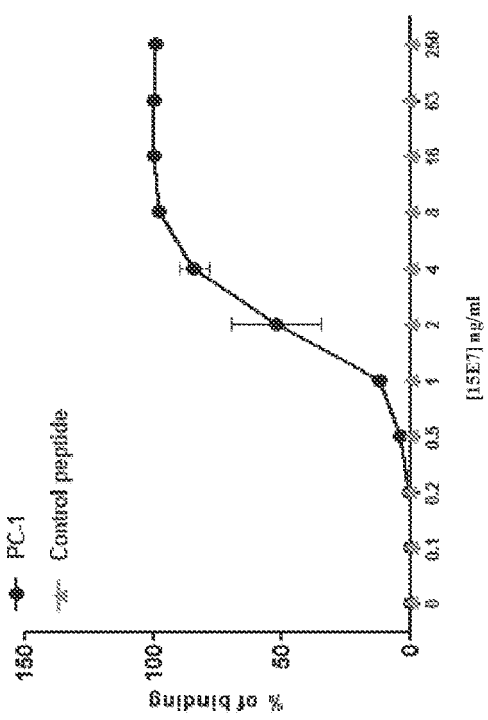
Figure 7C:
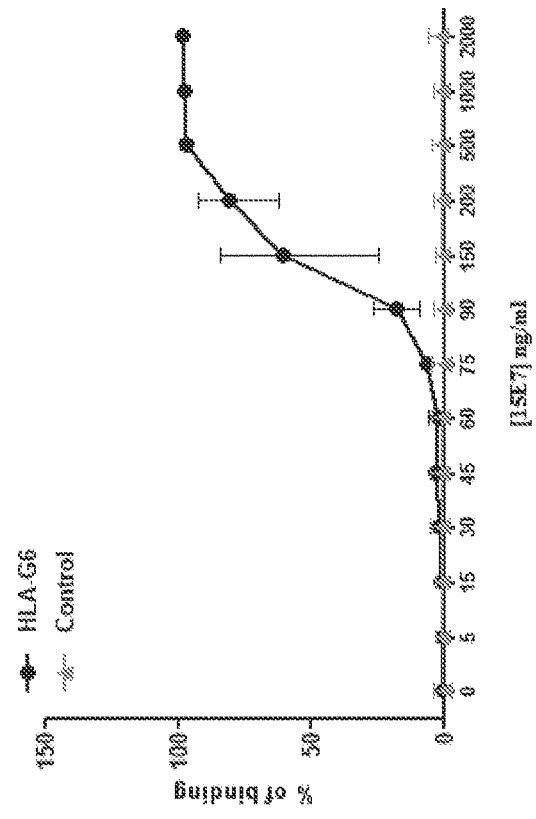

15E7 antibody was titrated by serial dilution on hβ2M-free HLA-G5; HLA-G6 and cPC-1 peptide coated beads as well as on their negative counterparts (uncoupled beads or beads coated with a mutated peptide). Results depicted in FIGS. 7A, 7B and 7C show that 15E7 strongly binds to the cPC-1 peptide with an $EC_{50}$ value of 2 ng/mL, to the recombinant HLA-G5 protein with an $EC_{50}$ value of 28 ng/mL and to the recombinant protein HLA-G6 with an $EC_{50}$ of 120 ng/mL, respectively. This analysis demonstrated the ability of 15E7 to bind specifically different β2M-free HLA-G isoforms.

Figure 8:
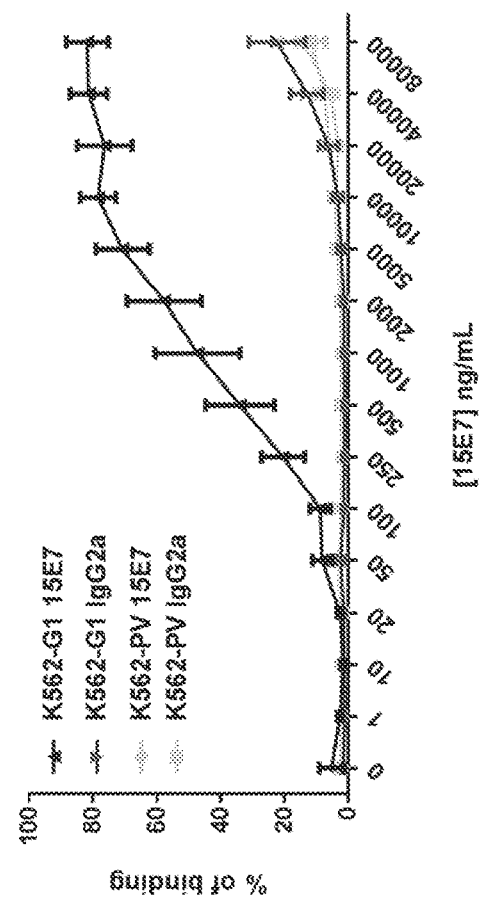
FIG. 8. Dose dependent binding of the anti-HLA-G monoclonal antibody 15E7 to β2M-free HLA-G1 expressed on K562 cell surface. Various concentrations (0-80 μg/mL) of 15E7 were used to determine the specific dose-dependent binding activity of 15E7 on HLA-G1 positive cells (K562-G1) vs. HLA-G negative control cells (K562-PV). The detection of 15E7 was carried out by flow cytometry using a PE-conjugated goat anti-mouse antibody. 15E7 exhibits a dose-dependent binding on the target K562-G1 cells (black line), whereas no binding was detected on the control cell line K562-PV (gray line).

The ability of 15E7 to bind β2M-free HLA-G1 isoform expressed on cell surface was also assessed. Indeed, K562-G1 expressing the HLA-G1 free isoform and K562-PV cells were incubated with serial dilutions of 15E7 antibody and specific binding was analyzed by flow cytometry in comparison to the isotype control (IgG2a). Results depicted in FIG. 8 show that 15E7 specifically binds to K562-G1 cells but not to K562-PV cells with an $EC_{50}$ value of 5.0 μg/mL.

Figure 9A:
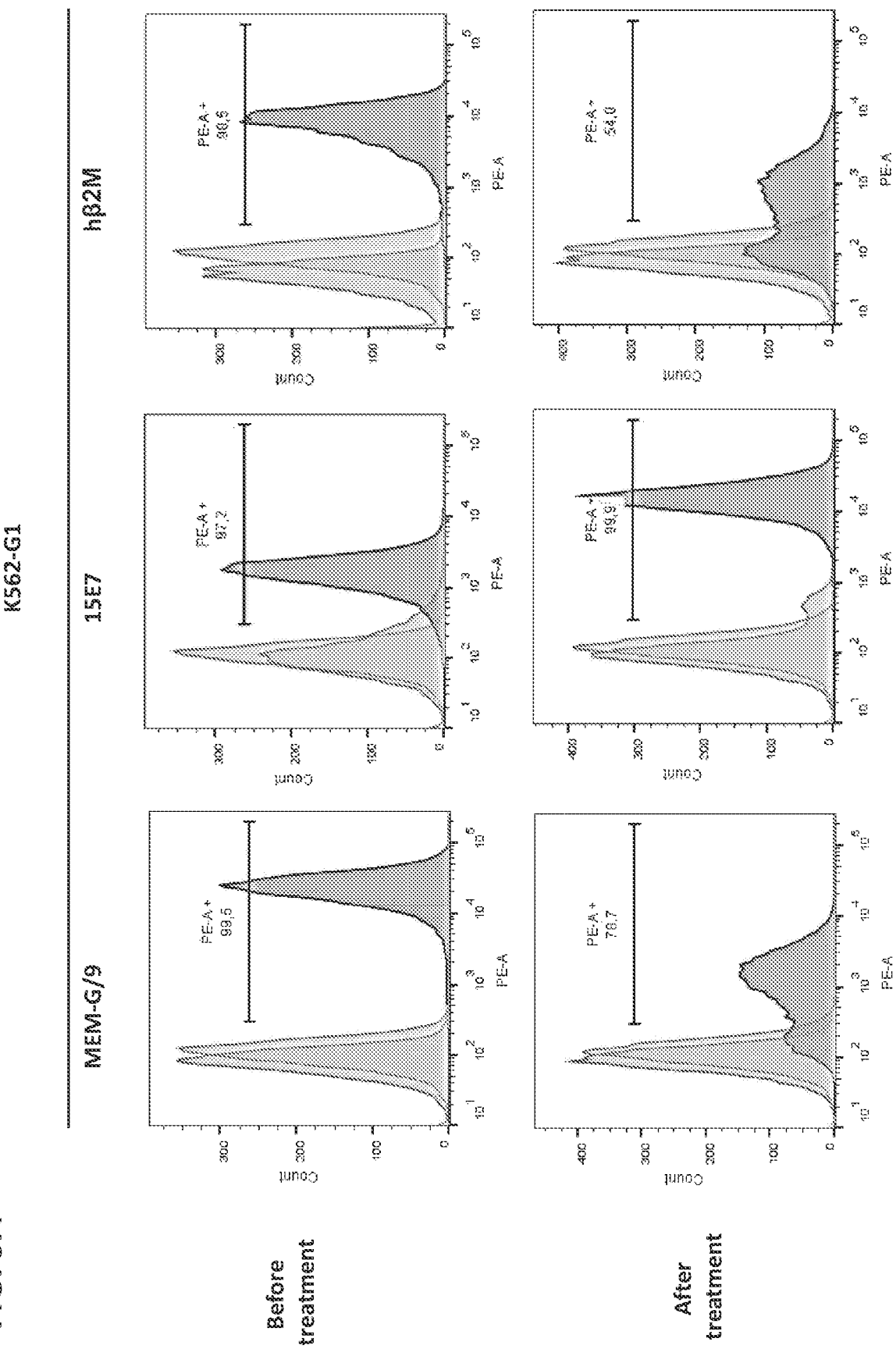
Figure 9B:
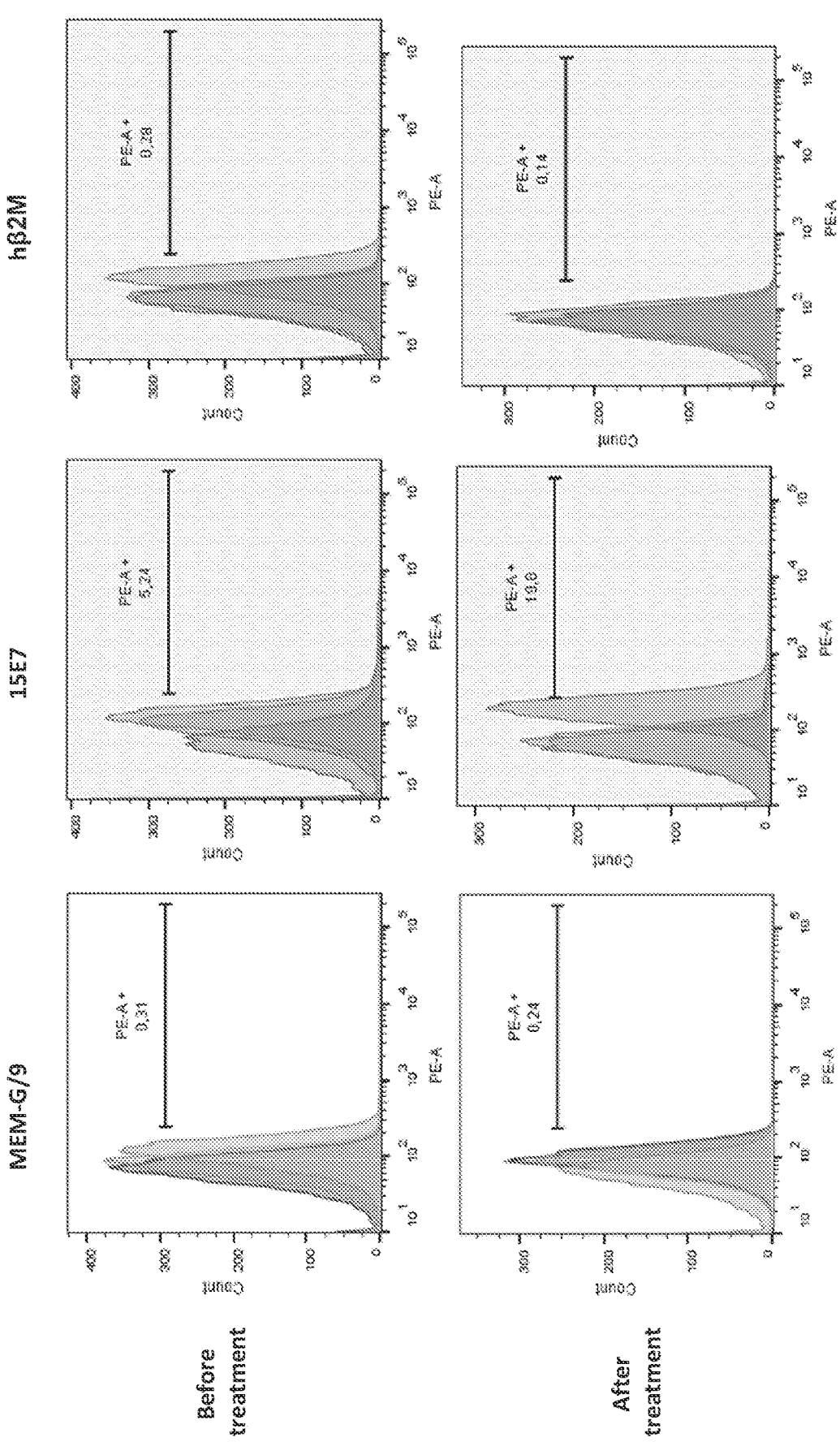

A mild acid treatment releases cell surface β2M molecules leaving HLA class I free heavy chains attached to the cell surface (Polakova et al., 1993; Storkus et al., 1993). The expression of HLA-G antigens on untreated and pH3.0 treated K562-G1 cells was analyzed by flow cytometry using MEM-G/9 mAb directed to native HLA-G/β2M complexes. In addition, a mAb directed against human β2m was used to control the experiment and validate the release of the latter. MEM-G/9 mAb as well as the anti-β2M mAb bind to untreated K562-G1 cells, however, acid treatment reduced their binding. By contrast, marking by 15E7 mAb increased demonstrating that it recognizes β2M free HLA-G heavy chains (FIG. 9A). K562-PV cells were used as negative control (FIG. 9B).

The same experiments were conducted on JEG-3 cells expressing the endogenous HLA-G1/β2M complex. 15E7 mAb didn't bind untreated JEG-3 cells, however the staining increased after acid treatment while the staining of MEM-G/9 and anti-β2M mAb dropped to near background values (FIG. 9C).

These results confirm that the 15E7 Mab recognizes the immunogenic cPC-1 peptide and an epitope expressed on cell surface HLA-G in the absence of β2M.

No Cross-Reactivity Towards Classical MHC Class I Molecules

As mentioned above, one of the main concerns in developing an anti-HLA-G monoclonal antibody was to obtain highly specific antibodies for HLA-G with no cross-reactivity towards classical MHC class I (MHC-I) molecules. The specificity of 15E7 to HLA-G and its absence of cross-reactivity with classical MHC-I molecules were evaluated by flow cytometry using different human MHC-I positive cell lines, which do not express HLA-G.

Figure 10:
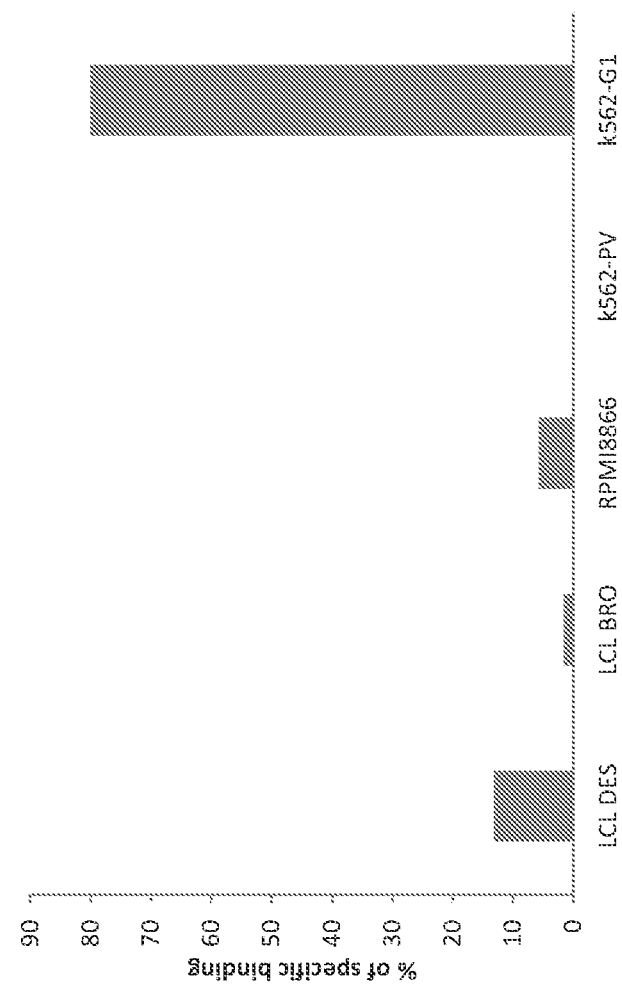
FIG. 10. The 15E7 monoclonal antibody binds specifically to HLA-G and not to classical MHC class I molecules. These binding assays assessing the specificity of 15E7 were performed using lymphoma cell lines (LCL DES, LCL BRO and RPMI8866) expressing human classical MHC class I molecules at their surface but not HLA-G, and analyzed by flow cytometry. 15E7 was used at a final concentration of 20 μg/mL. Binding is represented as a percentage of positive stained cells with 15E7 in comparison to the isotype control (IgG2a). K562-G1 and K562-PV cells were used as positive and negative controls, respectively.

Indeed, human lymphoma cell lines (LCL-DES, LCL-BRO and RPMI8866), expressing human classical MHC-I molecules but not HLA-G on their surface were stained with a fixed concentration of 15E7 (20 μg/mL; 133 nM). This concentration was used since 80% of K562-G1 cells were stained and no unspecific binding with the isotype control was detected at this dosage. K562-G1 and K562-PV cells were used as positive and negative controls, respectively. FIG. 10 shows that 15E7 strongly binds to HLA-G1 expressing cells (K562-G1) whereas HLA-G negative cells expressing classical MHC-I molecules were not stained. It demonstrates that 15E7 monoclonal antibody is specific to HLA-G proteins and does not present any cross-reactivity against classical MHC class I molecules.

DISCUSSION

The present work, shows how to produce anti-HLA-G antibodies based on a HLA-G peptide immunization approach. The peptide (PC-1) used for immunization was designed to be highly specific for HLA-G in comparison with classical MHC class I molecules and contains amino acids involved in the interaction of full length HLA-G with its receptors LILRB1 and LILRB2.

The inventors showed that, despite the hydrophobic properties of this HLA-G α3 region, it was possible to develop anti-HLA-G monoclonal antibodies using different technologies, fusion (generation of hybridomas) and phage display.

The anti-HLA-G antibodies described above are capable of recognizing several isoforms of HLA-G. These antibodies bind to endogenous cell surface β2M-free HLA-G1. As they do not cross-react with classical MHC class I molecules these HLA-G specific antibodies could be used for diagnostic and therapeutic purposes.

REFERENCES

Agaugue S, Carosella E D, Rouas-Freiss N. Role of HLA-G in tumor escape through expansion of myeloid-derived suppressor cells and cytokinic balance in favor of Th2—versus Th1/Th17. Blood 2011; 117: 7021-31.

Altschul S F, Gish W, Miller W, Myers E W, Lipman D J. Basic local alignment search tool. J Mol Biol 1990; 215:403-10.

Altschul S F, Madden T L, Schäffer A A, Zhang J, Zhang Z, Miller W, Lipman D J. Gapped BLAST and PSI-BLAST: a new generation of protein database search programs. Nucleic Acids Res 1997; 25:3389-402.

Blaschitz A, Hutter H, Leitner V, Pilz S, Wintersteiger R, Dohr G, Sedlmayr P. Reaction patterns of monoclonal antibodies to HLA-G in human tissues and on cell lines: a comparative study. Hum Immunol 2000; 61: 1074-85.

Carosella E D, et al., HLA-G: from biology to clinical benefits. Trends Immunol 2008; 29:125-32.

Carosella E D, et al., Beyond the increasing complexity of the immunomodulatory HLA-G molecule. Blood 2008; 111:4862-70.

Carosella E D, et al., HLA-G: An Immune Checkpoint Molecule. Adv Immunol 2015; 127:33-144.

Clements C S, Kjer-Nielsen L, Kostenko L, Hoare H L, Dunstone M A, Moses E, Freed K, Brooks A G, Rossjohn J, McCluskey J. Crystal structure of HLA-G: a nonclassical MHC class I molecule expressed at the fetal-maternal interface. Proc Natl Acad Sci USA 2005; 102: 3360-5.

Desai S A, et al., Structural relatedness of distinct determinants recognized by monoclonal antibody TP25.99 on beta 2-microglobulin-associated and beta 2-microglobulin-free HLA class I heavy chains. J Immunol 2000; 165:3275-83.

Ellis S A, Palmer M S, McMichael A J. Human trophoblast and the choriocarcinoma cell line BeWo express a truncated HLA Class I molecule. J Immunol 1990; 144: 731-5.

Favier, B., HoWangYin K Y, Wu J, Caumartin J, Daouya M, Horuzsko A, Carosella E D, LeMaoult J. Tolerogenic function of dimeric forms of HLA-G recombinant proteins: a comparative study in vivo. PLoS One 2011; 6: e21011.

Geraghty D E, Koller B H, Orr H R A human major histocompatibility complex class I gene that encodes a protein with a shortened cytoplasmic segment. Proc Natl Acad Sci USA 1987. 84: 9145-9.

HoWangYin K Y, Loustau M, Wu J, Alegre E, Daouya M, Caumartin J, Sousa S, Horuzsko A, Carosella E D, LeMaoult J. Multimeric structures of HLA-G isoforms function through differential binding to LILRB receptors. Cell Mol Life Sci 2012; 69:4041-9

Karlin S, Altschul S F. Methods for assessing the statistical significance of molecular sequence features by using general scoring schemes. Proc Natl Acad Sci USA 1990; 87:2264-8.

Karlin S, Altschul S F. Applications and statistics for multiple high-scoring segments in molecular sequences. Proc Natl Acad Sci USA 1993; 90:5873-7.

Lazar G A, Dang W, Karki S, Vafa O, Peng J S, Hyun L, Chan C, Chung H S, Eivazi A, Yoder S C, Vielmetter J, Carmichael D F, Hayes R J, Dahiyat B I. Engineered antibody Fc variants with enhanced effector function. Proc Natl Acad Sci USA. 2006; 103: 4005-4010.

Liang S, Baibakov B, Horuzsko A. HLA-G inhibits the functions of murine dendritic cells via the PIR-B immune inhibitory receptor. Eur J Immunol 2002; 32: 2418-26.

Menier C, et al., Characterization of monoclonal antibodies recognizing HLA-G or HLA-E: new tools to analyze the expression of nonclassical HLA class I molecules. Hum Immunol 2003; 64:315-26.

Moore G L, Chen H, Karki S, Lazar G A. Engineered Fc variant antibodies with enhanced ability to recruit complement and mediate effector functions. MAbs. 2010 March-April; 2(2):181-9.

Moy F J, et al., Analysis by NMR spectroscopy of the structural homology between the linear and the cyclic peptide recognized by anti-human leukocyte antigen class I monoclonal antibody TP25.99*. J Biol Chem 2000; 275:24679-85.

Naji A, et al., Binding of HLA-G to ITIM-bearing Ig-like transcript 2 receptor suppresses B cell responses. J Immunol 2014; 192:1536-46.

Polakova K, Karpatova M, Russ G. Dissociation of beta 2-microglobulin is responsible for selective reduction of HLA class I antigenicity following acid treatment of cells. Mol Immunol 1993; 30:1223-30.

Qiu J, et al., Soluble HLA-G expression and renal graft acceptance. Am J Transplant 2006; 6:2152-6.

Storkus W J, Zej H J, Salter R D, Lotze M T. Identification of T-cell epitopes: rapid isolation of class I-presented peptides from viable cells by mild acid elution. J Immunother Emphasis Tumor Immunol 1993; 14: 94-103.

Tanabe M, Sekimata M, Ferrone S, Takiguchi M. Structural and functional analysis of monomorphic determinants recognized by monoclonal antibodies reacting with the HLA class I alpha 3 domain. J Immunol 1992; 148:3202-9.

Tripathi P, Agrawal S. The role of human leukocyte antigen E and G in HIV infection. AIDS 2007; 21:1395-404

Yan W H, HLA-G expression in cancers: potential role in diagnosis, prognosis and therapy. Endocr Metab Immune Disord Drug Targets 2011; 11:76-89

What is claimed is:

1. A pharmaceutical composition comprising an anti-human leukocyte antigen G (HLA-G) antibody or an antigen-binding fragment thereof, and a pharmaceutical carrier; wherein the antibody or antigen-binding fragment comprises:
   (a) a heavy chain variable region (VH) comprising a heavy chain complementarity determining region 1 (HC CDR1) of SEQ ID NO: 8, a heavy chain complementarity determining region 2 (HC CDR2) of SEQ ID NO: 10, and a heavy chain complementarity determining region 3 (HC CDR3) of SEQ ID NO: 12; and
   (b) a light chain variable region (VL) comprising a light chain complementarity determining region 1 (LC CDR1) of SEQ ID NO: 2, a light chain complementarity determining region 2 (LC CDR2) of sequence KVS and a light chain complementarity determining region 3 (LC CDR3) of SEQ ID NO: 5.

2. The pharmaceutical composition of claim 1, wherein the VH comprises SEQ ID NO: 64 and the VL comprises SEQ ID NO: 63.

3. The pharmaceutical composition of claim 2, wherein the antibody is a full-length immunoglobulin G comprising two heavy chains and two light chains.

4. The pharmaceutical composition of claim 1, wherein the antibody or antigen-binding fragment is humanized or chimeric.

5. The pharmaceutical composition of claim 1, wherein the VH, the VL, or both the VH and VL comprise human immunoglobulin framework region sequences.

6. The pharmaceutical composition of claim 1, wherein the antibody comprises an immunoglobulin constant region.

7. The pharmaceutical composition of claim 1, wherein the antigen-binding fragment is a Fv, a dsFv, a scFv, a Fab, a Fab', or a F(ab')$_2$.

8. The pharmaceutical composition of claim 1, wherein the antibody is monoclonal.

9. The pharmaceutical composition of claim 1, wherein the antibody or antigen-binding fragment is linked to a cytotoxic agent.

* * * * *

SEQUENCE LISTING

<160> NUMBER OF SEQ ID NOS: 104

<210> SEQ ID NO 1
<211> LENGTH: 26
<212> TYPE: PRT
<213> ORGANISM: Mus musculus

<400> SEQUENCE: 1

Asp Val Leu Met Thr Gln Ile Pro Phe Ser Leu Pro Val Ser Leu Gly
1               5                   10                  15

Asp Gln Ala Ser Ile Ser Cys Arg Ser Ser
            20                  25

<210> SEQ ID NO 2
<211> LENGTH: 11
<212> TYPE: PRT
<213> ORGANISM: Mus musculus

<400> SEQUENCE: 2

Gln Ser Ile Val His Arg Ser Gly Asn Thr Tyr
1               5                   10

<210> SEQ ID NO 3
<211> LENGTH: 17
<212> TYPE: PRT
<213> ORGANISM: Mus musculus

<400> SEQUENCE: 3

Leu Glu Trp Tyr Leu Gln Lys Pro Gly Gln Ser Pro Lys Leu Leu Ile
1               5                   10                  15

Tyr

<210> SEQ ID NO 4
<211> LENGTH: 36
<212> TYPE: PRT
<213> ORGANISM: Mus musculus

<400> SEQUENCE: 4

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr Cys
        35

<210> SEQ ID NO 5
<211> LENGTH: 9
<212> TYPE: PRT
<213> ORGANISM: Mus musculus

<400> SEQUENCE: 5

Phe Gln Gly Ser His Leu Pro Pro Thr
1               5

<210> SEQ ID NO 6
<211> LENGTH: 9
<212> TYPE: PRT
<213> ORGANISM: Mus musculus

<400> SEQUENCE: 6

Phe Gly Gly Thr Thr Leu Glu Ile Lys
1               5

<210> SEQ ID NO 7
<211> LENGTH: 25
<212> TYPE: PRT
<213> ORGANISM: Mus musculus

<400> SEQUENCE: 7

Gln Val Gln Leu Gln Gln Pro Gly Ala Glu Leu Val Arg Pro Gly Ser
1               5                   10                  15

Ser Val Lys Leu Ser Cys Lys Ala Ser
            20                  25

<210> SEQ ID NO 8
<211> LENGTH: 8
<212> TYPE: PRT
<213> ORGANISM: Mus musculus

<400> SEQUENCE: 8

Gly Tyr Thr Phe Thr Asp Tyr Trp
1               5

<210> SEQ ID NO 9
<211> LENGTH: 17
<212> TYPE: PRT
<213> ORGANISM: Mus musculus

<400> SEQUENCE: 9

Met Asp Trp Val Lys Gln Arg Pro Gly Gln Gly Leu Glu Trp Ile Gly
1               5                   10                  15

Thr

<210> SEQ ID NO 10
<211> LENGTH: 8
<212> TYPE: PRT
<213> ORGANISM: Mus musculus

<400> SEQUENCE: 10

Ile Tyr Pro Ser Asp Ser Ser Thr
1               5

<210> SEQ ID NO 11
<211> LENGTH: 38
<212> TYPE: PRT
<213> ORGANISM: Mus musculus

<400> SEQUENCE: 11

His Tyr Asn Gln Glu Phe Lys Gly Lys Ala Thr Met Thr Val Asp Lys
1               5                   10                  15

Ser Ser Ser Thr Ala Tyr Met His Leu Ser Ser Leu Thr Ser Glu Asp
            20                  25                  30

Ser Ala Val Tyr Tyr Cys
            35

<210> SEQ ID NO 12
<211> LENGTH: 13
<212> TYPE: PRT
<213> ORGANISM: Mus musculus

<400> SEQUENCE: 12

Ala Arg Glu Gly Leu Ala Gly Val Phe Tyr Phe Asp Tyr
1               5                   10

<210> SEQ ID NO 13

```
<211> LENGTH: 11
<212> TYPE: PRT
<213> ORGANISM: Mus musculus

<400> SEQUENCE: 13

Trp Gly Gln Gly Thr Thr Leu Thr Val Ser Ser
1               5                   10

<210> SEQ ID NO 14
<211> LENGTH: 26
<212> TYPE: PRT
<213> ORGANISM: Mus musculus

<400> SEQUENCE: 14

Asp Val Leu Met Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 15
<211> LENGTH: 11
<212> TYPE: PRT
<213> ORGANISM: Mus musculus

<400> SEQUENCE: 15

Gln Ser Leu Val His Ser Asn Gly Asn Thr Tyr
1               5                   10

<210> SEQ ID NO 16
<211> LENGTH: 17
<212> TYPE: PRT
<213> ORGANISM: Mus musculus

<400> SEQUENCE: 16

Leu His Trp Tyr Leu Gln Lys Pro Gly Gln Ser Pro Lys Leu Leu Ile
1               5                   10                  15

Tyr

<210> SEQ ID NO 17
<211> LENGTH: 36
<212> TYPE: PRT
<213> ORGANISM: Mus musculus

<400> SEQUENCE: 17

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
            35

<210> SEQ ID NO 18
<211> LENGTH: 9
<212> TYPE: PRT
<213> ORGANISM: Mus musculus

<400> SEQUENCE: 18

Ser Gln Ser Thr His Phe Pro Pro Thr
1               5

<210> SEQ ID NO 19
<211> LENGTH: 10
<212> TYPE: PRT
```

<213> ORGANISM: Mus musculus

<400> SEQUENCE: 19

Phe Gly Gly Gly Thr Lys Leu Glu Ile Ile
1               5                   10

<210> SEQ ID NO 20
<211> LENGTH: 9
<212> TYPE: PRT
<213> ORGANISM: Mus musculus

<400> SEQUENCE: 20

Ser Gln Ser Thr His Val Pro Pro Thr
1               5

<210> SEQ ID NO 21
<211> LENGTH: 10
<212> TYPE: PRT
<213> ORGANISM: Mus musculus

<400> SEQUENCE: 21

Phe Gly Ala Gly Thr Lys Leu Glu Leu Lys
1               5                   10

<210> SEQ ID NO 22
<211> LENGTH: 25
<212> TYPE: PRT
<213> ORGANISM: Mus musculus

<400> SEQUENCE: 22

Gln Val Gln Leu Lys Gln Ser Gly Pro Gln Leu Val Arg Pro Gly Ala
1               5                   10                  15

Ser Val Lys Ile Pro Cys Lys Ala Ser
            20                  25

<210> SEQ ID NO 23
<211> LENGTH: 8
<212> TYPE: PRT
<213> ORGANISM: Mus musculus

<400> SEQUENCE: 23

Gly Tyr Ser Phe Thr Asn Tyr Trp
1               5

<210> SEQ ID NO 24
<211> LENGTH: 17
<212> TYPE: PRT
<213> ORGANISM: Mus musculus

<400> SEQUENCE: 24

Met His Trp Val Lys Gln Arg Pro Gly Gln Gly Leu Glu Trp Ile Gly
1               5                   10                  15

Met

<210> SEQ ID NO 25
<211> LENGTH: 8
<212> TYPE: PRT
<213> ORGANISM: Mus musculus

<400> SEQUENCE: 25

Ile Ala Pro Ser Asp Ser Asp Ser
1               5

```
<210> SEQ ID NO 26
<211> LENGTH: 38
<212> TYPE: PRT
<213> ORGANISM: Mus musculus

<400> SEQUENCE: 26

Arg Leu Asn Gln Asn Phe Lys Asp Lys Ala Thr Leu Thr Val Asp Lys
1               5                   10                  15

Ser Ser Ser Thr Ala Tyr Met Gln Leu Ser Ser Pro Thr Ser Glu Asp
            20                  25                  30

Ser Ala Val Tyr Tyr Cys
        35

<210> SEQ ID NO 27
<211> LENGTH: 14
<212> TYPE: PRT
<213> ORGANISM: Mus musculus

<400> SEQUENCE: 27

Ala Arg Glu Gly Val Thr Met Ile Thr Thr Gly Leu Asp Tyr
1               5                   10

<210> SEQ ID NO 28
<211> LENGTH: 11
<212> TYPE: PRT
<213> ORGANISM: Mus musculus

<400> SEQUENCE: 28

Trp Gly Gln Gly Thr Thr Leu Thr Val Ser Ser
1               5                   10

<210> SEQ ID NO 29
<211> LENGTH: 275
<212> TYPE: PRT
<213> ORGANISM: Homo sapiens

<400> SEQUENCE: 29

Gly Ser His Ser Met Arg Tyr Phe Ser Ala Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
    50                  55                  60

Arg Asn Thr Lys Ala His Ala Gln Thr Asp Arg Met Asn Leu Gln Thr
65                  70                  75                  80

Leu Arg Gly Tyr Tyr Asn Gln Ser Glu Ala Ser Ser His Thr Leu Gln
                85                  90                  95

Trp Met Ile Gly Cys Asp Leu Gly Ser Asp Gly Arg Leu Leu Arg Gly
            100                 105                 110

Tyr Glu Gln Tyr Ala Tyr Asp Gly Lys Asp Tyr Leu Ala Leu Asn Glu
        115                 120                 125

Asp Leu Arg Ser Trp Thr Ala Ala Asp Thr Ala Ala Gln Ile Ser Lys
    130                 135                 140

Arg Lys Cys Glu Ala Ala Asn Val Ala Glu Gln Arg Arg Ala Tyr Leu
145                 150                 155                 160

Glu Gly Thr Cys Val Glu Trp Leu His Arg Tyr Leu Glu Asn Gly Lys
                165                 170                 175
```

```
Glu Met Leu Gln Arg Ala Asp Pro Pro Lys Thr His Val Thr His His
            180                 185                 190

Pro Val Phe Asp Tyr Glu Ala Thr Leu Arg Cys Trp Ala Leu Gly Phe
        195                 200                 205

Tyr Pro Ala Glu Ile Ile Leu Thr Trp Gln Arg Asp Gly Glu Asp Gln
    210                 215                 220

Thr Gln Asp Val Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Met Leu
            260                 265                 270

Arg Trp Lys
        275

<210> SEQ ID NO 30
<211> LENGTH: 275
<212> TYPE: PRT
<213> ORGANISM: Homo sapiens

<400> SEQUENCE: 30

Gly Ser His Ser Leu Lys Tyr Phe His Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala Gly Ser His Thr Leu Gln
                85                  90                  95

Trp Met His Gly Cys Glu Leu Gly Pro Asp Gly Arg Phe Leu Arg Gly
            100                 105                 110

Tyr Glu Gln Phe Ala Tyr Asp Gly Lys Asp Tyr Leu Thr Leu Asn Glu
        115                 120                 125

Asp Leu Arg Ser Trp Thr Ala Val Asp Thr Ala Ala Gln Ile Ser Glu
    130                 135                 140

Gln Lys Ser Asn Asp Ala Ser Glu Ala Glu His Gln Arg Ala Tyr Leu
145                 150                 155                 160

Glu Asp Thr Cys Val Glu Trp Leu His Lys Tyr Leu Glu Lys Gly Lys
                165                 170                 175

Glu Thr Leu Leu His Leu Glu Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Gln Asp Gly Glu Gly His
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Val Thr Leu
            260                 265                 270
```

Arg Trp Lys
        275

<210> SEQ ID NO 31
<211> LENGTH: 275
<212> TYPE: PRT
<213> ORGANISM: Homo sapiens

<400> SEQUENCE: 31

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 32
<211> LENGTH: 275
<212> TYPE: PRT
<213> ORGANISM: Homo sapiens

<400> SEQUENCE: 32

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
            35                  40                  45

Ala Pro Trp Ile Glu Gln Glu Gly Pro Glu Tyr Trp Asp Arg Asn Thr
        50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 33
<211> LENGTH: 274
<212> TYPE: PRT
<213> ORGANISM: Homo sapiens

<400> SEQUENCE: 33

Gly Ser His Ser Met Arg Tyr Phe Cys Thr Ala Val Ser Arg Pro Gly
1               5                   10                  15

Arg Gly Glu Pro His Phe Ile Ala Val Gly Tyr Val Asp Asp Thr Gln
            20                  25                  30

Phe Val Arg Phe Asp Ser Asp Glu Ser Pro Arg Gly Glu Pro Arg
            35                  40                  45

Ala Pro Trp Val Glu Arg Lys Gly Pro Glu Tyr Trp Asp Arg Glu Thr
        50                  55                  60

Gln Lys Tyr Lys Pro Gln Ala Gln Thr Asp Arg Val Ser Leu Arg Asn
65                  70                  75                  80

Leu Arg Gly Tyr Tyr Asn Gln Ser Glu Ala Gly Ser His Ile Ile Arg
                85                  90                  95

Met Tyr Gly Cys Asp Val Gly Pro Asp Gly Arg Leu Leu Arg Gly Tyr
            100                 105                 110

Asp Gln His Ala Tyr Asp Gly Lys Asp Tyr Ile Ala Leu Asn Glu Asp

```
                    115                 120                 125
Leu Arg Ser Trp Thr Ala Ala Asn Thr Ala Ala Gln Ile Thr Gln Arg
            130                 135                 140

Lys Trp Glu Ala Ala Arg Glu Ala Glu Gln Leu Arg Ala Tyr Leu Glu
145                 150                 155                 160

Gly Leu Cys Val Glu Trp Leu Arg Arg Tyr Leu Lys Asn Gly Lys Glu
                165                 170                 175

Thr Leu Gln Gly Ala Glu His Pro Lys Thr His Val Thr His His Pro
            180                 185                 190

Val Ser Asp His Glu Ala Thr Leu Arg Cys Trp Ala Leu Gly Phe Tyr
        195                 200                 205

Pro Ala Glu Ile Thr Leu Thr Trp Gln Trp Asp Gly Glu Asp Gln Thr
    210                 215                 220

Gln Asp Thr Glu Leu Val Glu Thr Arg Pro Ala Gly Asp Gly Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Glu Pro Leu Thr Leu Arg
            260                 265                 270

Trp Glu

<210> SEQ ID NO 34
<211> LENGTH: 275
<212> TYPE: PRT
<213> ORGANISM: Homo sapiens

<400> SEQUENCE: 34

Gly Ser His Ser Met Arg Tyr Phe Tyr Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asn Leu Arg Thr
65                  70                  75                  80

Ala Ala Arg Tyr Tyr Asn Gln Ser Glu Ala Gly Ser His Ile Ile Gln
                85                  90                  95

Arg Met Tyr Gly Cys Asp Val Gly Pro Asp Gly Arg Leu Leu Arg Gly
            100                 105                 110

Tyr Asp Gln Asp Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Gly Leu Cys Val Glu Ser Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ser Leu Gly Phe
        195                 200                 205

Tyr Pro Ala Glu Ile Thr Leu Thr Trp Gln Arg Asp Gly Glu Asp Gln
```

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
            245                 250                 255

Tyr Thr Cys His Val Gln His Glu Gly Leu Pro Lys Pro Leu Thr Leu
            260                 265                 270

Arg Trp Glu
        275

<210> SEQ ID NO 35
<211> LENGTH: 336
<212> TYPE: DNA
<213> ORGANISM: Mus musculus

<400> SEQUENCE: 35
gatgttttga tgacccaaat tccattctcc ctgcctgtca gtcttggaga tcaagcctcc    60
atctcttgca gatctagtca gagcattgta catagaagtg aaacaccta tttagagtgg   120 tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatcttcct   300
ccgacgttcg gtggaggcac cacgctggaa atcaaa                            336

<210> SEQ ID NO 36
<211> LENGTH: 100
<212> TYPE: PRT
<213> ORGANISM: Mus musculus

<400> SEQUENCE: 36

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro
        100

<210> SEQ ID NO 37
<211> LENGTH: 12
<212> TYPE: PRT
<213> ORGANISM: Mus musculus

<400> SEQUENCE: 37

Trp Thr Phe Gly Gly Gly Thr Lys Leu Glu Ile Lys
1               5                   10

<210> SEQ ID NO 38
<211> LENGTH: 360
<212> TYPE: DNA
<213> ORGANISM: Mus musculus

<400> SEQUENCE: 38

| caggtccaac | tgcagcagcc | tggggctgaa | ctggtgaggc | ctgggtcttc | agtgaagctg | 60 |
| tcctgcaagg | cttctggcta | caccttcacc | gactactgga | tggattgggt | gaagcagagg | 120 |
| cctggacaag | gccttgaatg | gattggtacc | atttacccct | ctgatagttc | aactcactac | 180 |
| aatcaagagt | tcaagggcaa | ggccacaatg | actgtagaca | aatcctccag | cacagcctac | 240 |
| atgcatctca | gcagcctgac | atctgaggac | tctgcggtct | attactgtgc | aagagaggga | 300 |
| ctagctgggg | tgttctactt | tgactactgg | ggccaaggca | ccactctcac | agtctcctca | 360 |

<210> SEQ ID NO 39
<211> LENGTH: 98
<212> TYPE: PRT
<213> ORGANISM: Mus musculus

<400> SEQUENCE: 39

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Met Asp Trp Val Lys Gln Arg Pro Gly Gln Gly Leu Glu Trp Ile
        35                  40                  45

Gly Asn Ile Tyr Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg

<210> SEQ ID NO 40
<211> LENGTH: 15
<212> TYPE: PRT
<213> ORGANISM: Mus musculus

<400> SEQUENCE: 40

Tyr Phe Asp Tyr Trp Gly Gln Gly Thr Thr Leu Thr Val Ser Ser
1               5                   10                  15

<210> SEQ ID NO 41
<211> LENGTH: 336
<212> TYPE: DNA
<213> ORGANISM: Mus musculus

<400> SEQUENCE: 41

| gatgttttga | tgacccaaac | tccactctcc | ctgcctgtca | gtcttggaga | tcaagcctcc | 60 |
| atctcttgca | gatctagtca | gagccttgta | cacagtaatg | gaaacaccta | tttacattgg | 120 |
| tacctgcaga | agccaggcca | gtctccaaag | ctcctgatct | acaaagtctc | caaccgattt | 180 |
| tctggggtcc | ctgacaggtt | cagtggcagt | ggatcaggga | cagatttcac | actcaagatc | 240 |
| agcagagtgg | aggctgagga | tctgggagtt | tatttctgct | ctcaaagtac | acattttcct | 300 |
| ccgacgttcg | gtggaggcac | caagctggaa | atcata | | | 336 |

<210> SEQ ID NO 42
<211> LENGTH: 100
<212> TYPE: PRT
<213> ORGANISM: Mus musculus

<400> SEQUENCE: 42

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Ser Gln Ser
                85                  90                  95

Thr His Val Pro
            100

<210> SEQ ID NO 43
<211> LENGTH: 12
<212> TYPE: PRT
<213> ORGANISM: Mus musculus

<400> SEQUENCE: 43

Trp Thr Phe Gly Gly Gly Thr Lys Leu Glu Ile Lys
1               5                   10

<210> SEQ ID NO 44
<211> LENGTH: 372
<212> TYPE: DNA
<213> ORGANISM: Mus musculus

<400> SEQUENCE: 44
gatgttttga tgacccaaac tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttcct   300
cccacgttcg gtgctgggac caagctggag ctgaaacggg ctgatgctgc accaactgta   360
tccgcggccg ca                                                       372

<210> SEQ ID NO 45
<211> LENGTH: 12
<212> TYPE: PRT
<213> ORGANISM: Mus musculus

<400> SEQUENCE: 45

Leu Thr Phe Gly Ala Gly Thr Lys Leu Glu Leu Lys
1               5                   10

<210> SEQ ID NO 46
<211> LENGTH: 363
<212> TYPE: DNA
<213> ORGANISM: Mus musculus

<400> SEQUENCE: 46
caggtgcagc tgaagcagtc tgggcctcag ctggttaggc ctggggcttc agtgaagata    60
ccctgcaagg cttctggtta ctcattcacc aactactgga tgcactgggt gaagcagagg   120

```
cctggacaag gtcttgagtg gattggcatg attgctcctt ccgatagtga tagtaggtta    180
aatcagaatt tcaaggacaa ggccacattg actgtagaca atcctccag cacagcctac    240 atgcaactca gcagcccgac atctgaggac tctgcggtct attactgtgc aagagaggga    300
gttacaatga taacgacggg ccttgactac tggggccaag gcaccactct cacagtctcc    360
tca                                                                 363
```

<210> SEQ ID NO 47
<211> LENGTH: 98
<212> TYPE: PRT
<213> ORGANISM: Mus musculus

<400> SEQUENCE: 47

```
Gln Val Gln Leu Gln Gln Pro Gly Ala Glu Leu Val Lys Pro Gly Ala
1               5                   10                  15

Ser Val Lys Ile Ser Cys Lys Ala Ser Gly Tyr Thr Phe Thr Ser Tyr
                20                  25                  30

Trp Met Asn Trp Val Lys Gln Arg Pro Gly Gln Gly Leu Glu Trp Ile
            35                  40                  45

Gly Glu Ile Asp Pro Ser Asp Ser Tyr Thr Asn Asn Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg
```

<210> SEQ ID NO 48
<211> LENGTH: 8
<212> TYPE: PRT
<213> ORGANISM: Mus musculus

<400> SEQUENCE: 48

```
Pro Thr Ile Val Thr Ile Val Thr
1               5
```

<210> SEQ ID NO 49
<211> LENGTH: 15
<212> TYPE: PRT
<213> ORGANISM: Artificial Sequence
<220> FEATURE:
<223> OTHER INFORMATION: Immunogenic peptide
<220> FEATURE:
<221> NAME/KEY: MISC_FEATURE
<222> LOCATION: (1)..(1)
<223> OTHER INFORMATION: Xaa at position 1 is absent, cysteine or valine
<220> FEATURE:
<221> NAME/KEY: MISC_FEATURE
<222> LOCATION: (15)..(15)
<223> OTHER INFORMATION: Xaa at position 15 is absent or cysteine

<400> SEQUENCE: 49

```
Xaa Thr His His Pro Val Phe Asp Tyr Glu Ala Thr Leu Arg Xaa
1               5                   10                  15
```

<210> SEQ ID NO 50
<211> LENGTH: 4
<212> TYPE: PRT
<213> ORGANISM: Artificial Sequence
<220> FEATURE:
<223> OTHER INFORMATION: fragment of immunogenic peptide

```
<400> SEQUENCE: 50

Lys Thr His Val
1

<210> SEQ ID NO 51
<211> LENGTH: 5
<212> TYPE: PRT
<213> ORGANISM: Artificial Sequence
<220> FEATURE:
<223> OTHER INFORMATION: fragment of immunogenic sequence

<400> SEQUENCE: 51

Cys Lys Thr His Val
1               5

<210> SEQ ID NO 52
<211> LENGTH: 15
<212> TYPE: PRT
<213> ORGANISM: Artificial Sequence
<220> FEATURE:
<223> OTHER INFORMATION: immunogenic peptide

<400> SEQUENCE: 52

Cys Thr His His Pro Val Phe Asp Tyr Glu Ala Thr Leu Arg Cys
1               5                   10                  15

<210> SEQ ID NO 53
<211> LENGTH: 19
<212> TYPE: PRT
<213> ORGANISM: Artificial Sequence
<220> FEATURE:
<223> OTHER INFORMATION: immunogenic peptide

<400> SEQUENCE: 53

Cys Lys Thr His Val Thr His His Pro Val Phe Asp Tyr Glu Ala Thr
1               5                   10                  15

Leu Arg Cys

<210> SEQ ID NO 54
<211> LENGTH: 13
<212> TYPE: PRT
<213> ORGANISM: Homo sapiens

<400> SEQUENCE: 54

Thr His His Pro Val Phe Asp Tyr Glu Ala Thr Leu Arg
1               5                   10

<210> SEQ ID NO 55
<211> LENGTH: 14
<212> TYPE: PRT
<213> ORGANISM: Homo sapiens

<400> SEQUENCE: 55

Thr His His Pro Val Phe Asp Tyr Glu Ala Thr Leu Arg Cys
1               5                   10

<210> SEQ ID NO 56
<211> LENGTH: 15
<212> TYPE: PRT
<213> ORGANISM: Homo sapiens

<400> SEQUENCE: 56

Val Thr His His Pro Val Phe Asp Tyr Glu Ala Thr Leu Arg Cys
1               5                   10                  15
```

```
<210> SEQ ID NO 57
<211> LENGTH: 14
<212> TYPE: PRT
<213> ORGANISM: Homo sapiens

<400> SEQUENCE: 57

Val Thr His His Pro Val Phe Asp Tyr Glu Ala Thr Leu Arg
1               5                   10

<210> SEQ ID NO 58
<211> LENGTH: 14
<212> TYPE: PRT
<213> ORGANISM: Artificial Sequence
<220> FEATURE:
<223> OTHER INFORMATION: immunogenic peptide

<400> SEQUENCE: 58

Cys Thr His His Pro Val Phe Asp Tyr Glu Ala Thr Leu Arg
1               5                   10

<210> SEQ ID NO 59
<211> LENGTH: 17
<212> TYPE: PRT
<213> ORGANISM: Homo sapiens

<400> SEQUENCE: 59

Lys Thr His Val Thr His His Pro Val Phe Asp Tyr Glu Ala Thr Leu
1               5                   10                  15

Arg

<210> SEQ ID NO 60
<211> LENGTH: 18
<212> TYPE: PRT
<213> ORGANISM: Homo sapiens

<400> SEQUENCE: 60

Lys Thr His Val Thr His His Pro Val Phe Asp Tyr Glu Ala Thr Leu
1               5                   10                  15

Arg Cys

<210> SEQ ID NO 61
<211> LENGTH: 18
<212> TYPE: PRT
<213> ORGANISM: Artificial Sequence
<220> FEATURE:
<223> OTHER INFORMATION: immunogenic peptide

<400> SEQUENCE: 61

Cys Lys Thr His Val Thr His His Pro Val Phe Asp Tyr Glu Ala Thr
1               5                   10                  15

Leu Arg

<210> SEQ ID NO 62
<211> LENGTH: 15
<212> TYPE: PRT
<213> ORGANISM: Artificial Sequence
<220> FEATURE:
<223> OTHER INFORMATION: mutant peptide

<400> SEQUENCE: 62

Cys Thr His His Pro Val Ala Asp Ala Glu Ala Thr Leu Arg Cys
1               5                   10                  15
```

-continued

```
<210> SEQ ID NO 63
<211> LENGTH: 111
<212> TYPE: PRT
<213> ORGANISM: Mus musculus

<400> SEQUENCE: 63

Asp Val Leu Met Thr Gln Ile Pro Phe Ser Leu Pro Val Ser Leu Gly
1               5                   10                  15

Asp Gln Ala Ser Ile Ser Cys Arg Ser Ser Gln Ser Ile Val His Arg
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Pro Thr Phe Gly Gly Thr Thr Leu Glu Ile Lys
            100                 105                 110

<210> SEQ ID NO 64
<211> LENGTH: 120
<212> TYPE: PRT
<213> ORGANISM: Mus musculus

<400> SEQUENCE: 64

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Asp Tyr
            20                  25                  30

Trp Met Asp Trp Val Lys Gln Arg Pro Gly Gln Gly Leu Glu Trp Ile
        35                  40                  45

Gly Thr Ile Tyr Pro Ser Asp Ser Ser Thr His Tyr Asn Gln Glu Phe
    50                  55                  60

Lys Gly Lys Ala Thr Met Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Glu Gly Leu Ala Gly Val Phe Tyr Phe Asp Tyr Trp Gly Gln
            100                 105                 110

Gly Thr Thr Leu Thr Val Ser Ser
        115                 120

<210> SEQ ID NO 65
<211> LENGTH: 112
<212> TYPE: PRT
<213> ORGANISM: Mus musculus

<400> SEQUENCE: 65

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Pro Thr Phe Gly Gly Gly Thr Lys Leu Glu Ile Ile
            100                 105                 110

<210> SEQ ID NO 66
<211> LENGTH: 112
<212> TYPE: PRT
<213> ORGANISM: Mus musculus

<400> SEQUENCE: 66

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ala Gly Thr Lys Leu Glu Leu Lys
            100                 105                 110

<210> SEQ ID NO 67
<211> LENGTH: 121
<212> TYPE: PRT
<213> ORGANISM: Mus musculus

<400> SEQUENCE: 67

Gln Val Gln Leu Lys Gln Ser Gly Pro Gln Leu Val Arg Pro Gly Ala
1               5                   10                  15

Ser Val Lys Ile Pro Cys Lys Ala Ser Gly Tyr Ser Phe Thr Asn Tyr
                20                  25                  30

Trp Met His Trp Val Lys Gln Arg Pro Gly Gln Gly Leu Glu Trp Ile
            35                  40                  45

Gly Met Ile Ala Pro Ser Asp Ser Asp Ser Arg Leu Asn Gln Asn Phe
        50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Glu Gly Val Thr Met Ile Thr Thr Gly Leu Asp Tyr Trp Gly
            100                 105                 110

Gln Gly Thr Thr Leu Thr Val Ser Ser
        115                 120

<210> SEQ ID NO 68
<211> LENGTH: 26
<212> TYPE: PRT
<213> ORGANISM: Mus musculus

<400> SEQUENCE: 68

```
Glu Asn Val Leu Thr Gln Ser Pro Ala Ile Met Ala Ala Ser Leu Gly
1               5                   10                  15

Glu Lys Val Thr Met Thr Cys Ser Ala Ser
            20                  25
```

<210> SEQ ID NO 69
<211> LENGTH: 7
<212> TYPE: PRT
<213> ORGANISM: Mus musculus

<400> SEQUENCE: 69

```
Ser Ser Val Ser Ser Asn Phe
1               5
```

<210> SEQ ID NO 70
<211> LENGTH: 17
<212> TYPE: PRT
<213> ORGANISM: Mus musculus

<400> SEQUENCE: 70

```
Leu His Trp Tyr Gln Gln Lys Ser Gly Thr Ser Pro Lys Leu Trp Ile
1               5                   10                  15

Tyr
```

<210> SEQ ID NO 71
<211> LENGTH: 36
<212> TYPE: PRT
<213> ORGANISM: Mus musculus

<400> SEQUENCE: 71

```
Asn Leu Ala Ser Gly Val Pro Ala Arg Phe Ser Gly Ser Gly Thr Gly
1               5                   10                  15

Ile Ser Tyr Ser Leu Thr Val Ser Asn Met Glu Ala Glu Asn Asp Ala
            20                  25                  30

Ala Tyr Tyr Cys
        35
```

<210> SEQ ID NO 72
<211> LENGTH: 9
<212> TYPE: PRT
<213> ORGANISM: Mus musculus

<400> SEQUENCE: 72

```
Gln Gln Trp Asn Ala Tyr Pro Phe Thr
1               5
```

<210> SEQ ID NO 73
<211> LENGTH: 25
<212> TYPE: PRT
<213> ORGANISM: Mus musculus

<400> SEQUENCE: 73

```
Glu Val Lys Leu Glu Glu Ser Gly Gly Gly Leu Val Gln Pro Gly Gly
1               5                   10                  15

Ser Met Lys Leu Ser Cys Val Ala Ser
            20                  25
```

<210> SEQ ID NO 74
<211> LENGTH: 8
<212> TYPE: PRT
<213> ORGANISM: Mus musculus

<400> SEQUENCE: 74

```
Gly Phe Thr Phe Ser Ser Tyr Trp
1               5
```

<210> SEQ ID NO 75
<211> LENGTH: 17
<212> TYPE: PRT
<213> ORGANISM: Mus musculus

<400> SEQUENCE: 75

```
Leu Ser Trp Val Arg Gln Ser Pro Glu Lys Gly Leu Glu Trp Val Ala
1               5                   10                  15

Glu
```

<210> SEQ ID NO 76
<211> LENGTH: 10
<212> TYPE: PRT
<213> ORGANISM: Mus musculus

<400> SEQUENCE: 76

```
Val Arg Leu Lys Ser Asp Asn Tyr Ala Thr
1               5                   10
```

<210> SEQ ID NO 77
<211> LENGTH: 38
<212> TYPE: PRT
<213> ORGANISM: Mus musculus

<400> SEQUENCE: 77

```
Ser Tyr Ala Glu Ser Val Lys Gly Lys Phe Thr Ile Ser Arg Asp Asp
1               5                   10                  15

Ala Asn Ser Arg Leu Tyr Leu Gln Met Asn Ser Leu Arg Pro Glu Asp
            20                  25                  30

Thr Gly Ile Tyr Tyr Cys
        35
```

<210> SEQ ID NO 78
<211> LENGTH: 5
<212> TYPE: PRT
<213> ORGANISM: Mus musculus

<400> SEQUENCE: 78

```
Thr Thr Gly Asp Tyr
1               5
```

<210> SEQ ID NO 79
<211> LENGTH: 25
<212> TYPE: PRT
<213> ORGANISM: Mus musculus

<400> SEQUENCE: 79

```
Asp Val Val Met Thr Gln Ile Pro Leu Ser Leu Pro Val Ser Leu Gly
1               5                   10                  15

Asp Gln Ala Ser Ile Ser Cys Arg Ser
            20                  25
```

<210> SEQ ID NO 80
<211> LENGTH: 11
<212> TYPE: PRT
<213> ORGANISM: Mus musculus

<400> SEQUENCE: 80

```
Gln Ser Leu Val Asn Ser Asn Gly Asn Thr Leu
```

-continued

```
<210> SEQ ID NO 81
<211> LENGTH: 9
<212> TYPE: PRT
<213> ORGANISM: Mus musculus

<400> SEQUENCE: 81

Ser Gln Ser Thr His Val Pro Trp Thr
1               5

<210> SEQ ID NO 82
<211> LENGTH: 10
<212> TYPE: PRT
<213> ORGANISM: Mus musculus

<400> SEQUENCE: 82

Phe Gly Gly Gly Thr Lys Leu Glu Ile Lys
1               5                   10

<210> SEQ ID NO 83
<211> LENGTH: 8
<212> TYPE: PRT
<213> ORGANISM: Mus musculus

<400> SEQUENCE: 83

Gly Leu Thr Phe Ser Ser Tyr Trp
1               5

<210> SEQ ID NO 84
<211> LENGTH: 17
<212> TYPE: PRT
<213> ORGANISM: Mus musculus

<400> SEQUENCE: 84

Met Ser Trp Val Arg Gln Ser Pro Glu Lys Gly Leu Glu Trp Val Ala
1               5                   10                  15

Glu

<210> SEQ ID NO 85
<211> LENGTH: 10
<212> TYPE: PRT
<213> ORGANISM: Mus musculus

<400> SEQUENCE: 85

Ile Arg Leu Arg Ser Asp Asn Tyr Val Lys
1               5                   10

<210> SEQ ID NO 86
<211> LENGTH: 38
<212> TYPE: PRT
<213> ORGANISM: Mus musculus

<400> SEQUENCE: 86

Gln Tyr Ala Asp Ser Val Lys Gly Arg Phe Thr Ile Ser Arg Asp Asp
1               5                   10                  15

Ser Lys Gly Arg Leu Tyr Leu Gln Met Asn Arg Leu Arg Gly Asp Asp
            20                  25                  30

Thr Gly Ile Tyr Phe Cys
        35

<210> SEQ ID NO 87
<211> LENGTH: 11
```

```
<212> TYPE: PRT
<213> ORGANISM: Mus musculus

<400> SEQUENCE: 87

Gln Thr Ile Val His Ser Asn Gly Asn Thr Tyr
1               5                   10

<210> SEQ ID NO 88
<211> LENGTH: 9
<212> TYPE: PRT
<213> ORGANISM: Mus musculus

<400> SEQUENCE: 88

Phe Gln Gly Ser His Val Pro Pro Thr
1               5

<210> SEQ ID NO 89
<211> LENGTH: 25
<212> TYPE: PRT
<213> ORGANISM: Mus musculus

<400> SEQUENCE: 89

Glu Val Gln Leu Gln Gln Ser Gly Ala Glu Leu Val Lys Pro Gly Thr
1               5                   10                  15

Ser Val Lys Leu Ser Cys Lys Ala Ser
            20                  25

<210> SEQ ID NO 90
<211> LENGTH: 8
<212> TYPE: PRT
<213> ORGANISM: Mus musculus

<400> SEQUENCE: 90

Gly Tyr Thr Phe Thr Arg Asn Trp
1               5

<210> SEQ ID NO 91
<211> LENGTH: 17
<212> TYPE: PRT
<213> ORGANISM: Mus musculus

<400> SEQUENCE: 91

Ile Thr Trp Val Arg Leu Arg Pro Gly Gln Gly Leu Glu Trp Ile Gly
1               5                   10                  15

Asp

<210> SEQ ID NO 92
<211> LENGTH: 8
<212> TYPE: PRT
<213> ORGANISM: Mus musculus

<400> SEQUENCE: 92

Ile Tyr Pro Gly Asp Ala Ser Thr
1               5

<210> SEQ ID NO 93
<211> LENGTH: 38
<212> TYPE: PRT
<213> ORGANISM: Mus musculus

<400> SEQUENCE: 93

His Tyr Asn Gly Lys Phe Lys Asn Lys Ala Thr Leu Thr Val Asp Thr
1               5                   10                  15
```

Ser Ser Ser Thr Ala Tyr Leu Gln Val Ser Ser Leu Thr Ser Glu Asp
            20                  25                  30

Ser Ala Val Tyr Tyr Cys
            35

<210> SEQ ID NO 94
<211> LENGTH: 13
<212> TYPE: PRT
<213> ORGANISM: Mus musculus

<400> SEQUENCE: 94

Ala Arg Glu Gln Val Gln Phe Ala Met Phe Phe Asp Val
1               5                   10

<210> SEQ ID NO 95
<211> LENGTH: 11
<212> TYPE: PRT
<213> ORGANISM: Mus musculus

<400> SEQUENCE: 95

Trp Gly Thr Gly Ala Thr Val Thr Val Ser Ser
1               5                   10

<210> SEQ ID NO 96
<211> LENGTH: 25
<212> TYPE: PRT
<213> ORGANISM: Mus musculus

<400> SEQUENCE: 96

Gln Val Gln Leu Gln Gln Pro Arg Ala Glu Leu Val Lys Pro Gly Ala
1               5                   10                  15

Ser Val Lys Met Ser Cys Lys Ala Ser
            20                  25

<210> SEQ ID NO 97
<211> LENGTH: 8
<212> TYPE: PRT
<213> ORGANISM: Mus musculus

<400> SEQUENCE: 97

Gly Tyr Thr Phe Ala Arg Tyr Trp
1               5

<210> SEQ ID NO 98
<211> LENGTH: 17
<212> TYPE: PRT
<213> ORGANISM: Mus musculus

<400> SEQUENCE: 98

Ile Ser Trp Leu Lys Leu Arg Pro Gly Gln Gly Leu Glu Trp Ile Gly
1               5                   10                  15

Asp

<210> SEQ ID NO 99
<211> LENGTH: 8
<212> TYPE: PRT
<213> ORGANISM: Mus musculus

<400> SEQUENCE: 99

Ile Tyr Pro Gly Asp Asp Ser Thr
1               5

<210> SEQ ID NO 100

```
<211> LENGTH: 38
<212> TYPE: PRT
<213> ORGANISM: Mus musculus

<400> SEQUENCE: 100

His Tyr Asn Gly Lys Phe Lys Asn Lys Ala Thr Leu Thr Val Asp Thr
1               5                   10                  15

Ser Thr Ser Thr Ala Tyr Ile Gln Leu Ser Ser Leu Thr Ser Glu Asp
            20                  25                  30

Ser Ala Val Tyr Tyr Cys
        35

<210> SEQ ID NO 101
<211> LENGTH: 11
<212> TYPE: PRT
<213> ORGANISM: Mus musculus

<400> SEQUENCE: 101

Gln Ser Ile Val His Ser Asn Gly Asn Thr Tyr
1               5                   10

<210> SEQ ID NO 102
<211> LENGTH: 38
<212> TYPE: PRT
<213> ORGANISM: Mus musculus

<400> SEQUENCE: 102

His Tyr Asn Gln Glu Phe Lys Gly Lys Ala Thr Met Thr Val Asp Lys
1               5                   10                  15

Ser Ser Ser Thr Ala Tyr Met His Leu Gly Ser Leu Thr Ser Glu Asp
            20                  25                  30

Ser Ala Val Tyr Tyr Cys
        35

<210> SEQ ID NO 103
<211> LENGTH: 18
<212> TYPE: PRT
<213> ORGANISM: artificial
<220> FEATURE:
<223> OTHER INFORMATION: Immunogenic peptide
<220> FEATURE:
<221> NAME/KEY: MISC_FEATURE
<222> LOCATION: (18)..(18)
<223> OTHER INFORMATION: Xaa at position 18 is absent or cysteine

<400> SEQUENCE: 103

Lys Thr His Val Thr His His Pro Val Phe Asp Tyr Glu Ala Thr Leu
1               5                   10                  15

Arg Xaa

<210> SEQ ID NO 104
<211> LENGTH: 19
<212> TYPE: PRT
<213> ORGANISM: artificial
<220> FEATURE:
<223> OTHER INFORMATION: Immunogenic peptide
<220> FEATURE:
<221> NAME/KEY: MISC_FEATURE
```

```
<222> LOCATION: (19)..(19)
<223> OTHER INFORMATION: Xaa at position 19 is absent or cysteine

<400> SEQUENCE: 104

Cys Lys Thr His Val Thr His His Pro Val Phe Asp Tyr Glu Ala Thr
1               5                   10                  15

Leu Arg Xaa
```